United States Patent
Burns et al.

(10) Patent No.: US 12,350,064 B2
(45) Date of Patent: *Jul. 8, 2025

(54) DETECTION OF TISSUE DAMAGE

(71) Applicant: Bruin Biometrics, LLC, Los Angeles, CA (US)

(72) Inventors: Martin F. Burns, Los angeles, CA (US); Graham O. Ross, Oceanside, CA (US)

(73) Assignee: Bruin Biometrics, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/630,787

(22) Filed: Apr. 9, 2024

(65) Prior Publication Data

US 2024/0268753 A1    Aug. 15, 2024

Related U.S. Application Data

(63) Continuation of application No. 18/047,084, filed on Oct. 17, 2022, now Pat. No. 11,980,475, which is a (Continued)

(51) Int. Cl.
*A61B 5/053* (2021.01)
*A61B 5/00* (2006.01)
(Continued)

(52) U.S. Cl.
CPC ............ *A61B 5/447* (2013.01); *A61B 5/0531* (2013.01); *A61B 5/0537* (2013.01); *A61B 5/443* (2013.01);
(Continued)

(58) Field of Classification Search
CPC ..... A61B 5/0531; A61B 5/0537; A61B 5/447; A61B 5/6843; A61B 2562/0214; A61B 2562/043; A61B 5/443; A61B 5/445; A61B 5/4836; A61B 5/7282; A61B 2560/0468; A61B 2562/046; A61B 5/4875; A61B 5/6801; A61B 5/7278; A61B 5/742;
(Continued)

(56) References Cited

U.S. PATENT DOCUMENTS

| 3,851,641 A | 12/1974 | Toole et al. |
| 4,295,009 A | 10/1981 | Weidler |

(Continued)

FOREIGN PATENT DOCUMENTS

| AU | 2020103438 A4 | 1/2021 |
| CA | 2811609 | 11/2011 |

(Continued)

OTHER PUBLICATIONS

Avci et al., "Low-Level Laser (Light) Therapy (LLLT) in Skin: Stimulating, Healing, Restoring," *Seminars in Cutaneous Medicine and Surgery*, 32(1):41-52 (Mar. 2013).

(Continued)

*Primary Examiner* — Jon Eric C Morales
(74) *Attorney, Agent, or Firm* — Arnold & Porter Kaye Scholer LLP

(57) ABSTRACT

Methods and apparatus for detection of tissue damage in patients using a medical device for an extended period of time are disclosed.

19 Claims, 9 Drawing Sheets

Related U.S. Application Data continuation of application No. 16/271,040, filed on Feb. 8, 2019, now Pat. No. 11,471,094.

(60) Provisional application No. 62/628,676, filed on Feb. 9, 2018.

(51) Int. Cl.

| | |
|---|---|
| *A61B 5/0531* | (2021.01) |
| *A61B 5/0537* | (2021.01) |
| *A61F 5/055* | (2006.01) |
| *A61F 5/44* | (2006.01) |
| *A61J 15/00* | (2006.01) |
| *A61M 5/172* | (2006.01) |
| *A61M 16/04* | (2006.01) |
| *A61M 16/06* | (2006.01) |
| *A61M 25/00* | (2006.01) |

(52) U.S. Cl.
CPC .......... *A61B 5/4836* (2013.01); *A61B 5/6843* (2013.01); *A61B 5/7282* (2013.01); *A61F 5/055* (2013.01); *A61F 5/44* (2013.01); *A61J 15/0003* (2013.01); *A61J 15/0084* (2015.05); *A61M 5/1723* (2013.01); *A61M 16/0465* (2013.01); *A61M 16/0497* (2013.01); *A61M 16/0666* (2013.01); *A61M 25/0017* (2013.01); *A61B 2562/0214* (2013.01); *A61B 2562/043* (2013.01)

(58) Field of Classification Search
CPC ... A61B 5/746; A61J 15/0003; A61J 15/0084; A61M 16/0666; A61M 16/0497; A61M 5/1723; A61M 16/0605; A61H 2201/5056; A61H 2205/12; A61H 2201/1697; A61H 2201/5051; A61H 9/0078
See application file for complete search history.

(56) References Cited

U.S. PATENT DOCUMENTS

| | | |
|---|---|---|
| 4,557,271 A | 12/1985 | Stoller et al. |
| 4,857,716 A | 8/1989 | Gombrich et al. |
| 4,860,753 A | 8/1989 | Amerena |
| 5,001,436 A | 3/1991 | Scot |
| 5,073,126 A | 12/1991 | Kikuchi et al. |
| 5,152,296 A | 10/1992 | Simons |
| 5,284,150 A | 2/1994 | Butterfield et al. |
| 5,292,341 A | 3/1994 | Snell |
| 5,367,789 A | 11/1994 | Lamont |
| 5,815,416 A | 9/1998 | Liebmann et al. |
| 5,904,581 A | 5/1999 | Pope et al. |
| 6,185,452 B1 | 2/2001 | Schulman |
| 6,204,749 B1 | 3/2001 | Ishihara |
| 6,223,088 B1 | 4/2001 | Scharnberg et al. |
| 6,254,435 B1 | 7/2001 | Cheong et al. |
| 6,312,263 B1 | 11/2001 | Higuchi et al. |
| 6,330,479 B1 | 12/2001 | Stauffer |
| 6,368,284 B1 | 4/2002 | Bardy |
| 6,370,426 B1 | 4/2002 | Campbell et al. |
| 6,434,422 B1 | 8/2002 | Tomoda et al. |
| 6,577,700 B1 | 6/2003 | Fan et al. |
| 6,634,045 B1 | 10/2003 | DuDonis et al. |
| 6,738,798 B1 | 5/2004 | Ploetz et al. |
| 6,756,793 B2 | 6/2004 | Hirono et al. |
| 6,963,772 B2 | 11/2005 | Bloom et al. |
| 7,079,899 B2 | 7/2006 | Petrofsky |
| 7,291,023 B1 | 11/2007 | Still et al. |
| 7,315,767 B2 | 1/2008 | Caduff et al. |
| 7,402,135 B2 | 7/2008 | Leveque et al. |
| 7,783,344 B2 | 8/2010 | Lackey et al. |
| 8,011,041 B2 | 9/2011 | Hann |
| 8,060,315 B2 | 11/2011 | Brosette et al. |
| 8,355,925 B2 | 1/2013 | Rothman et al. |
| 8,390,583 B2 | 3/2013 | Forutanpour et al. |
| 8,494,617 B2 | 7/2013 | Baker, Jr. et al. |
| 8,648,707 B2 | 2/2014 | Franz et al. |
| 8,690,785 B2 | 4/2014 | Lading |
| 8,724,833 B1 | 5/2014 | Shain et al. |
| 8,925,392 B2 | 1/2015 | Esposito et al. |
| 9,028,407 B1 | 5/2015 | Bennett-Guerrero |
| 9,095,305 B2 | 8/2015 | Engler et al. |
| 9,220,455 B2 | 12/2015 | Sarrafzadeh et al. |
| 9,271,676 B2 | 3/2016 | Alanen et al. |
| 9,398,879 B2 | 7/2016 | Sarrafzadeh et al. |
| 9,675,289 B2 | 6/2017 | Heaton |
| 9,763,596 B2 | 9/2017 | Tonar et al. |
| 9,949,683 B2 | 4/2018 | Afentakis |
| 9,980,673 B2 | 5/2018 | Sarrafzadeh et al. |
| 10,085,643 B2 | 10/2018 | Bandic et al. |
| 10,126,340 B2 | 11/2018 | Simmons |
| 10,166,387 B2 | 1/2019 | Bergelin et al. |
| 10,178,961 B2 | 1/2019 | Tonar et al. |
| 10,182,740 B2 | 1/2019 | Tonar et al. |
| 10,188,340 B2 | 1/2019 | Sarrafzadeh et al. |
| 10,194,856 B2 | 2/2019 | Afentakis et al. |
| 10,206,604 B2 | 2/2019 | Bergelin et al. |
| 10,226,187 B2 | 3/2019 | Al-Ali et al. |
| 10,278,636 B2 | 5/2019 | Wu et al. |
| 10,285,898 B2 | 5/2019 | Douglas et al. |
| 10,307,060 B2 | 6/2019 | Tran |
| 10,342,482 B1 | 7/2019 | Lisy et al. |
| 10,383,527 B2 | 8/2019 | Al-Ali |
| 10,420,602 B2 | 9/2019 | Horton et al. |
| 10,441,185 B2 | 10/2019 | Rogers et al. |
| 10,448,844 B2 | 10/2019 | Al-Ali et al. |
| 10,463,293 B2 | 11/2019 | Maharbiz et al. |
| 10,485,447 B2 | 11/2019 | Tonar et al. |
| 10,898,129 B2 | 1/2021 | Burns et al. |
| 10,950,960 B2 | 3/2021 | Burns et al. |
| 10,959,664 B2 | 3/2021 | Burns et al. |
| 11,172,871 B2 | 11/2021 | Bly et al. |
| 11,191,477 B2 | 12/2021 | Burns |
| 11,253,192 B2 | 2/2022 | Sarrafzadeh et al. |
| 11,284,810 B2 | 3/2022 | Tonar et al. |
| 11,304,652 B2 | 4/2022 | Burns et al. |
| 11,337,651 B2 | 5/2022 | Burns et al. |
| 11,342,696 B2 | 5/2022 | Burns et al. |
| 11,426,118 B2 | 8/2022 | Burns |
| 11,471,094 B2 * | 10/2022 | Burns ................. A61M 5/1723 |
| 11,534,077 B2 | 12/2022 | Tonar et al. |
| 11,600,939 B2 | 3/2023 | Burns et al. |
| 11,627,910 B2 | 4/2023 | Burns et al. |
| 11,642,075 B2 | 5/2023 | Burns et al. |
| 11,779,265 B2 | 10/2023 | Sarrafzadeh et al. |
| 11,824,291 B2 | 11/2023 | Burns et al. |
| 11,832,929 B2 | 12/2023 | Tonar et al. |
| 11,980,475 B2 * | 5/2024 | Burns ................. A61M 5/1723 |
| 12,097,041 B2 | 9/2024 | Burns et al. |
| 12,132,271 B2 | 10/2024 | Burns et al. |
| 2001/0049609 A1 | 12/2001 | Girouard et al. |
| 2001/0051783 A1 | 12/2001 | Edwards et al. |
| 2002/0016535 A1 | 2/2002 | Martin et al. |
| 2002/0032485 A1 | 3/2002 | Flam et al. |
| 2002/0070866 A1 | 6/2002 | Newham |
| 2002/0112898 A1 | 8/2002 | Honda et al. |
| 2002/0143262 A1 | 10/2002 | Bardy |
| 2003/0009244 A1 | 1/2003 | Engleson et al. |
| 2003/0036674 A1 | 2/2003 | Bouton |
| 2003/0036713 A1 | 2/2003 | Bouton et al. |
| 2003/0110662 A1 | 6/2003 | Gilman et al. |
| 2003/0116447 A1 | 6/2003 | Surridge et al. |
| 2003/0130427 A1 | 7/2003 | Cleary et al. |
| 2003/0139255 A1 * | 7/2003 | Lina .................... A61H 9/0078 482/24 |
| 2003/0199783 A1 | 10/2003 | Bloom et al. |
| 2004/0041029 A1 | 3/2004 | Postman et al. |
| 2004/0046668 A1 | 3/2004 | Smith et al. |
| 2004/0054298 A1 | 3/2004 | Masuo et al. |
| 2004/0080325 A1 | 4/2004 | Ogura |
| 2004/0133092 A1 | 7/2004 | Kain |

(56) References Cited

U.S. PATENT DOCUMENTS

| | | |
|---|---|---|
| 2004/0147977 A1 | 7/2004 | Petrofsky |
| 2004/0171962 A1 | 9/2004 | Leveque et al. |
| 2004/0176754 A1 | 9/2004 | Island et al. |
| 2004/0236200 A1 | 11/2004 | Say et al. |
| 2004/0254457 A1 | 12/2004 | Van Der Weide |
| 2005/0027175 A1 | 2/2005 | Yang |
| 2005/0049658 A1 | 3/2005 | Connors et al. |
| 2005/0070778 A1 | 3/2005 | Lackey et al. |
| 2005/0086072 A1 | 4/2005 | Fox, Jr. et al. |
| 2005/0096513 A1 | 5/2005 | Ozguz et al. |
| 2005/0177061 A1 | 8/2005 | Alanen et al. |
| 2005/0203435 A1 | 9/2005 | Nakada |
| 2005/0215918 A1 | 9/2005 | Frantz et al. |
| 2005/0245795 A1 | 11/2005 | Goode et al. |
| 2005/0251418 A1 | 11/2005 | Fox et al. |
| 2006/0052678 A1 | 3/2006 | Drinan et al. |
| 2006/0058593 A1 | 3/2006 | Drinan et al. |
| 2006/0097949 A1 | 5/2006 | Luebke et al. |
| 2006/0206013 A1 | 9/2006 | Rothman et al. |
| 2006/0239547 A1 | 10/2006 | Robinson et al. |
| 2007/0043282 A1 | 2/2007 | Mannheimer et al. |
| 2007/0051362 A1 | 3/2007 | Sullivan et al. |
| 2007/0106172 A1 | 5/2007 | Abreu |
| 2007/0179585 A1 | 8/2007 | Chandler et al. |
| 2007/0185392 A1 | 8/2007 | Sherman et al. |
| 2007/0191273 A1 | 8/2007 | Ambati et al. |
| 2007/0213700 A1 | 9/2007 | Davison et al. |
| 2007/0248542 A1 | 10/2007 | Kane et al. |
| 2008/0009764 A1 | 1/2008 | Davies |
| 2008/0015894 A1 | 1/2008 | Miller et al. |
| 2008/0027509 A1 | 1/2008 | Andino et al. |
| 2008/0039700 A1 | 2/2008 | Drinan et al. |
| 2008/0048680 A1 | 2/2008 | Hargreaves et al. |
| 2008/0054276 A1 | 3/2008 | Vogel et al. |
| 2008/0063363 A1 | 3/2008 | Kientz et al. |
| 2008/0166268 A1 | 7/2008 | Yamaguchi et al. |
| 2008/0259577 A1 | 10/2008 | Hu et al. |
| 2008/0278336 A1 | 11/2008 | Ortega et al. |
| 2009/0047694 A1 | 2/2009 | Shuber |
| 2009/0054752 A1 | 2/2009 | Jonnalagadda et al. |
| 2009/0076410 A1 | 3/2009 | Libbus et al. |
| 2009/0104797 A1 | 4/2009 | Tseng et al. |
| 2009/0124924 A1 | 5/2009 | Eror et al. |
| 2009/0189092 A1 | 7/2009 | Aoi et al. |
| 2009/0209830 A1 | 8/2009 | Nagle et al. |
| 2009/0285785 A1 | 11/2009 | Jimi et al. |
| 2009/0306487 A1 | 12/2009 | Crowe et al. |
| 2009/0326346 A1 | 12/2009 | Kracker et al. |
| 2010/0017182 A1 | 1/2010 | Voros et al. |
| 2010/0030167 A1 | 2/2010 | Thirstrup et al. |
| 2010/0042389 A1 | 2/2010 | Farruggia et al. |
| 2010/0073170 A1 | 3/2010 | Siejko et al. |
| 2010/0113979 A1 | 5/2010 | Sarrafzadeh et al. |
| 2010/0152551 A1 | 6/2010 | Hsu et al. |
| 2010/0268111 A1 | 10/2010 | Drinan et al. |
| 2010/0298687 A1 | 11/2010 | Yoo et al. |
| 2010/0312076 A1 | 12/2010 | Bly et al. |
| 2010/0312233 A1 | 12/2010 | Furnish et al. |
| 2010/0324455 A1 | 12/2010 | Rangel et al. |
| 2010/0324611 A1 | 12/2010 | Deming et al. |
| 2011/0015697 A1 | 1/2011 | McAdams |
| 2011/0046505 A1 | 2/2011 | Cornish et al. |
| 2011/0160548 A1 | 6/2011 | Forster |
| 2011/0175844 A1 | 7/2011 | Berggren |
| 2011/0184264 A1 | 7/2011 | Galasso, Jr. et al. |
| 2011/0191122 A1 | 8/2011 | Kharraz Tavakol et al. |
| 2011/0223078 A1 | 9/2011 | Ohashi |
| 2011/0237926 A1 | 9/2011 | Jensen |
| 2011/0263950 A1 | 10/2011 | Larson et al. |
| 2011/0301441 A1 | 12/2011 | Bandic et al. |
| 2011/0313311 A1 | 12/2011 | Gaw |
| 2012/0029410 A1 | 2/2012 | Koenig et al. |
| 2012/0061257 A1 | 3/2012 | Yu et al. |
| 2012/0078088 A1 | 3/2012 | Whitestone et al. |
| 2012/0083672 A1 | 4/2012 | Cui et al. |
| 2012/0150011 A1 | 6/2012 | Besio |
| 2012/0179006 A1 | 7/2012 | Jansen et al. |
| 2012/0190989 A1 | 7/2012 | Kaiser et al. |
| 2012/0271121 A1 | 10/2012 | Della Torre et al. |
| 2013/0041235 A1 | 2/2013 | Rogers et al. |
| 2013/0072870 A1 | 3/2013 | Heppe et al. |
| 2013/0121544 A1 | 5/2013 | Sarrafzadeh et al. |
| 2013/0123587 A1 | 5/2013 | Sarrafzadeh et al. |
| 2013/0137951 A1 | 5/2013 | Chuang et al. |
| 2013/0253285 A1 | 9/2013 | Bly et al. |
| 2013/0261496 A1 | 10/2013 | Engler et al. |
| 2013/0301255 A1 | 11/2013 | Kim et al. |
| 2013/0310440 A1 | 11/2013 | Duskin et al. |
| 2013/0333094 A1 | 12/2013 | Rogers et al. |
| 2013/0338661 A1 | 12/2013 | Behnke, II |
| 2014/0121479 A1 | 5/2014 | O'Connor et al. |
| 2014/0142984 A1 | 5/2014 | Wright et al. |
| 2014/0200486 A1 | 7/2014 | Bechtel et al. |
| 2014/0221792 A1 | 8/2014 | Miller et al. |
| 2014/0273025 A1 | 9/2014 | Hurskainen et al. |
| 2014/0275823 A1 | 9/2014 | Lane et al. |
| 2014/0288397 A1 | 9/2014 | Sarrafzadeh et al. |
| 2014/0298928 A1 | 10/2014 | Duesterhoft et al. |
| 2014/0316297 A1 | 10/2014 | McCaughan et al. |
| 2014/0318699 A1 | 10/2014 | Longinotti-Buitoni et al. |
| 2015/0002168 A1 | 1/2015 | Kao et al. |
| 2015/0009168 A1 | 1/2015 | Levesque et al. |
| 2015/0094548 A1 | 4/2015 | Sabatini et al. |
| 2015/0157435 A1 | 6/2015 | Chasins et al. |
| 2015/0186607 A1 | 7/2015 | Gileijnse et al. |
| 2015/0230863 A1 | 8/2015 | Youngquist et al. |
| 2015/0343173 A1 | 12/2015 | Tobescu et al. |
| 2015/0363567 A1 | 12/2015 | Pettus |
| 2015/0366499 A1 | 12/2015 | Sarrafzadeh et al. |
| 2015/0371522 A1 | 12/2015 | Mravyan et al. |
| 2016/0015962 A1 | 1/2016 | Shokoueinejad Maragheh et al. |
| 2016/0038055 A1 | 2/2016 | Wheeler et al. |
| 2016/0058342 A1 | 3/2016 | Maiz-Aguinaga et al. |
| 2016/0072308 A1 | 3/2016 | Nyberg et al. |
| 2016/0081580 A1 | 3/2016 | Bergelin et al. |
| 2016/0100790 A1 | 4/2016 | Cantu et al. |
| 2016/0101282 A1 | 4/2016 | Bergelin et al. |
| 2016/0166438 A1 | 6/2016 | Rovaniemi |
| 2016/0174631 A1 | 6/2016 | Tong et al. |
| 2016/0174871 A1 | 6/2016 | Sarrafzadeh et al. |
| 2016/0220172 A1 | 8/2016 | Sarrafzadeh et al. |
| 2016/0270672 A1 | 9/2016 | Chen et al. |
| 2016/0270968 A1 | 9/2016 | Stanford et al. |
| 2016/0278692 A1 | 9/2016 | Larson et al. |
| 2016/0296268 A1 | 10/2016 | Gee et al. |
| 2016/0310034 A1 | 10/2016 | Tonar et al. |
| 2016/0338591 A1 | 11/2016 | Lachenbruch et al. |
| 2016/0374588 A1 | 12/2016 | Shariff |
| 2017/0007153 A1 | 1/2017 | Tonar et al. |
| 2017/0014044 A1* | 1/2017 | Tonar .................. A61B 5/742 |
| 2017/0014045 A1 | 1/2017 | Tonar et al. |
| 2017/0105646 A1 | 4/2017 | Bryenton et al. |
| 2017/0156658 A1 | 6/2017 | Maharbiz et al. |
| 2017/0172489 A1 | 6/2017 | Afentakis |
| 2017/0188841 A1 | 7/2017 | Ma et al. |
| 2017/0238849 A1 | 8/2017 | Chapman et al. |
| 2017/0245799 A1 | 8/2017 | Fleischer et al. |
| 2017/0255812 A1 | 9/2017 | Kwon |
| 2017/0311807 A1 | 11/2017 | Fu et al. |
| 2017/0319066 A1 | 11/2017 | Ver Steeg |
| 2017/0319073 A1 | 11/2017 | DiMaio et al. |
| 2018/0020058 A1 | 1/2018 | Martines et al. |
| 2018/0045725 A1 | 2/2018 | Yoo et al. |
| 2018/0220924 A1 | 8/2018 | Burns et al. |
| 2018/0220953 A1 | 8/2018 | Burns et al. |
| 2018/0220954 A1 | 8/2018 | Burns et al. |
| 2018/0220961 A1 | 8/2018 | Burns et al. |
| 2018/0360344 A1 | 12/2018 | Burns et al. |
| 2019/0000352 A1 | 1/2019 | Everett et al. |
| 2019/0038133 A1 | 2/2019 | Tran |
| 2019/0053751 A1 | 2/2019 | Torres |
| 2019/0060602 A1 | 2/2019 | Tran et al. |
| 2019/0069836 A1 | 3/2019 | Hettrick |
| 2019/0104981 A1 | 4/2019 | Sarrafzadeh et al. |

(56) References Cited

U.S. PATENT DOCUMENTS

| | | |
|---|---|---|
| 2019/0104982 A1 | 4/2019 | Dunn et al. |
| 2019/0117964 A1 | 4/2019 | Bahrami et al. |
| 2019/0134396 A1 | 5/2019 | Toth et al. |
| 2019/0142333 A1 | 5/2019 | Burns et al. |
| 2019/0147990 A1 | 5/2019 | Burns et al. |
| 2019/0148901 A1 | 5/2019 | Komoto |
| 2019/0150882 A1 | 5/2019 | Maharbiz et al. |
| 2019/0175098 A1 | 6/2019 | Burns et al. |
| 2019/0192066 A1 | 6/2019 | Schoess et al. |
| 2019/0246972 A1 | 8/2019 | Burns et al. |
| 2019/0282436 A1 | 9/2019 | Douglas et al. |
| 2019/0290189 A1 | 9/2019 | Sarrafzadeh et al. |
| 2019/0307360 A1 | 10/2019 | Tonar et al. |
| 2019/0307405 A1 | 10/2019 | Terry et al. |
| 2020/0008299 A1 | 1/2020 | Tran et al. |
| 2020/0043607 A1 | 2/2020 | Zerhusen et al. |
| 2020/0069240 A1 | 3/2020 | Burns |
| 2020/0069241 A1 | 3/2020 | Burns |
| 2020/0069242 A1 | 3/2020 | Burns et al. |
| 2020/0077892 A1 | 3/2020 | Tran |
| 2020/0078499 A1 | 3/2020 | Gadde et al. |
| 2020/0093395 A1 | 3/2020 | Tonar et al. |
| 2020/0100723 A1 | 4/2020 | Burns |
| 2020/0113488 A1 | 4/2020 | Al-Ali et al. |
| 2020/0127398 A1 | 4/2020 | Burns et al. |
| 2020/0296821 A1 | 9/2020 | Trublowski et al. |
| 2020/0297244 A1 | 9/2020 | Brownhill et al. |
| 2020/0297255 A1 | 9/2020 | Martinez et al. |
| 2021/0076974 A1 | 3/2021 | Burns |
| 2021/0159621 A1 | 5/2021 | Burns et al. |
| 2021/0204864 A1 | 7/2021 | Burns et al. |
| 2021/0307635 A1 | 10/2021 | Burns |
| 2022/0071555 A1 | 3/2022 | Burns et al. |
| 2022/0192587 A1 | 6/2022 | Burns et al. |
| 2022/0211291 A1 | 7/2022 | Tonar et al. |
| 2022/0240840 A1 | 8/2022 | Burns |
| 2022/0273238 A1 | 9/2022 | Burns et al. |
| 2022/0285865 A1 | 9/2022 | Burns et al. |
| 2022/0287584 A1 | 9/2022 | Burns et al. |
| 2022/0330847 A1 | 10/2022 | Burns et al. |
| 2022/0409086 A1 | 12/2022 | Burns |
| 2023/0068683 A1 | 3/2023 | Burns et al. |
| 2023/0109698 A1 | 4/2023 | Tonar et al. |
| 2023/0148893 A1 | 5/2023 | Burns et al. |
| 2023/0363698 A9 | 5/2023 | Burns |
| 2023/0337966 A1 | 6/2023 | Sarrafzadeh et al. |
| 2023/0240592 A1 | 8/2023 | Burns et al. |
| 2023/0329629 A1 | 10/2023 | Burns et al. |
| 2023/0335929 A1 | 10/2023 | Burns et al. |
| 2023/0346240 A1 | 11/2023 | Tonar et al. |
| 2024/0039192 A1 | 2/2024 | Burns et al. |
| 2024/0081727 A1 | 3/2024 | Burns |
| 2024/0138696 A1 | 5/2024 | Burns et al. |
| 2024/0225529 A1 | 7/2024 | Burns |
| 2024/0389932 A1 | 11/2024 | Burns et al. |
| 2025/0023263 A1 | 1/2025 | Burns et al. |

FOREIGN PATENT DOCUMENTS

| | | |
|---|---|---|
| CA | 2609842 C | 10/2016 |
| CN | 102033166 A | 4/2011 |
| CN | 204119175 U | 1/2015 |
| CN | 104352230 A | 2/2015 |
| CN | 104567657 A | 4/2015 |
| CN | 104644125 A | 5/2015 |
| CN | 105578333 A | 5/2016 |
| CN | 105963074 A | 9/2016 |
| CN | 208111467 U | 11/2018 |
| DE | 102012011212 A1 | 12/2012 |
| EP | 0970656 A1 | 1/2000 |
| EP | 1080687 A1 | 3/2001 |
| EP | 1372475 B1 | 1/2004 |
| EP | 1569553 A1 | 9/2005 |
| EP | 3092946 A1 | 11/2016 |
| EP | 3280488 B1 | 12/2018 |
| GB | 2148513 | 5/1985 |
| GB | 2584808 A | 12/2020 |
| JP | H06-502323 | 3/1994 |
| JP | H10-201726 | 8/1998 |
| JP | 2000-060805 A | 2/2000 |
| JP | 2001-178705 | 7/2001 |
| JP | 2001-326773 A | 11/2001 |
| JP | 2003-169787 A | 6/2003 |
| JP | 2003-169788 A | 6/2003 |
| JP | 2003-202312 | 7/2003 |
| JP | 2003-290166 A | 10/2003 |
| JP | 2005-52227 | 3/2005 |
| JP | 2009-268611 A | 11/2009 |
| JP | 4418419 | 2/2010 |
| JP | 2013-198639 A | 10/2013 |
| JP | 2015-134074 | 7/2015 |
| KR | 10-2014-0058445 | 5/2014 |
| WO | 1996/010951 A1 | 4/1996 |
| WO | 2001/054580 A1 | 8/2001 |
| WO | 2002/080770 A1 | 10/2002 |
| WO | 2004/105602 A1 | 12/2004 |
| WO | 2005/099644 A2 | 10/2005 |
| WO | 2006/029035 A1 | 3/2006 |
| WO | 2007/098762 A1 | 9/2007 |
| WO | 2009/144615 A1 | 12/2009 |
| WO | 2010/060102 A2 | 5/2010 |
| WO | 2011/004165 A1 | 1/2011 |
| WO | 2011/022418 A2 | 2/2011 |
| WO | 2011/048556 A2 | 4/2011 |
| WO | 2011/080080 A1 | 7/2011 |
| WO | 2011/080262 A1 | 7/2011 |
| WO | 2011/084722 A1 | 7/2011 |
| WO | 2011/091517 A1 | 8/2011 |
| WO | 2011/143071 A2 | 11/2011 |
| WO | 2013/033724 A1 | 3/2013 |
| WO | 2013/114356 A1 | 8/2013 |
| WO | 2013/116242 A2 | 8/2013 |
| WO | 2013/140714 A1 | 9/2013 |
| WO | 2014/186894 A1 | 11/2014 |
| WO | 2015/003015 A2 | 1/2015 |
| WO | 2015/022583 A2 | 2/2015 |
| WO | 2015/077838 A1 | 6/2015 |
| WO | 2015/168720 A1 | 11/2015 |
| WO | 2015/169911 A1 | 11/2015 |
| WO | 2015/195720 A1 | 12/2015 |
| WO | 2016/098062 A1 | 6/2016 |
| WO | 2016/172263 A1 | 10/2016 |
| WO | 2016/172264 A1 | 10/2016 |
| WO | 2017/032393 | 3/2017 |
| WO | 2017/214188 A1 | 12/2017 |
| WO | 2017/218818 A2 | 12/2017 |
| WO | 2018/071715 A1 | 4/2018 |
| WO | 2018/077560 A1 | 5/2018 |
| WO | 2018/115461 A1 | 6/2018 |
| WO | 2018/144938 | 8/2018 |
| WO | 2018/144941 | 8/2018 |
| WO | 2018/144943 | 8/2018 |
| WO | 2018/144946 | 8/2018 |
| WO | 2018/168424 A1 | 9/2018 |
| WO | 2018/189265 A1 | 10/2018 |
| WO | 2018/209100 A1 | 11/2018 |
| WO | 2018/234443 A1 | 12/2018 |
| WO | 2018/236739 | 12/2018 |
| WO | 2019/020551 A1 | 1/2019 |
| WO | 2019/030384 A2 | 2/2019 |
| WO | 2019/048624 A1 | 3/2019 |
| WO | 2019/048626 A1 | 3/2019 |
| WO | 2019/048638 A1 | 3/2019 |
| WO | 2019/072531 A1 | 4/2019 |
| WO | 2019/073389 A1 | 4/2019 |
| WO | 2019/076967 A2 | 4/2019 |
| WO | 2019/096828 A1 | 5/2019 |
| WO | 2019/099810 A1 | 5/2019 |
| WO | 2019/099812 A1 | 5/2019 |
| WO | 2019/113481 | 6/2019 |
| WO | 2019/157290 | 8/2019 |
| WO | 2019/162272 A1 | 8/2019 |
| WO | 2020/014779 A1 | 1/2020 |
| WO | 2020/043806 A1 | 3/2020 |

(56) References Cited

FOREIGN PATENT DOCUMENTS

| WO | 2020/053290 A1 | 3/2020 |
|---|---|---|
| WO | 2020/077100 A1 | 4/2020 |
| WO | 2020/187643 A1 | 9/2020 |
| WO | 2020/187851 A1 | 9/2020 |
| WO | 2020/234429 A2 | 11/2020 |

OTHER PUBLICATIONS

Brunetti et al., "Validation of a sub-ebidermal moisture scanner for early detection of pressure ulcers in an ex vivo procine model of localized oedema," *J. Tissue Viability*, 32(4):508-515 (available online Jul. 8, 2023).
Byrne et al., "Sub epidermal moisture measurement and targeted SSKIN bundle interventions, a winning combination for the treatment of early pressure ulcer development," *Int. Wound J.*, 2022:1-13 (published online Nov. 25, 2022).
Chan et al., "Using Wireless Measuring Devices and Tablet PC to Improve the Efficiency of Vital Signs Data Collection in Hospital," 4 pp., 2014 IEEE International Symposium on Bioelectronics and Bioinformatics (IEEE ISBB 2014).
Extended European Search Report dated Jun. 11, 2024, in European Patent Application No. 24158801.1.
International Search Report mailed May 29, 2024, issued in International Patent Application PCT/US2023/074190.
Lustig et al., "A machine learning algorithm for early detection of heel deep tissue injuries based on daily histroy of sub-epidermal moisture measurements," *Int. Wound J.*, 2021:1-10 (published online Dec. 1, 2021).
Partial European Search Report completed Mar. 27, 2024, in European Patent Application No. 23208591.0.
Partial European Search Report completed Apr. 16, 2024, in European Patent Application No. 24151800.0.
Supplementary European Search Report completed May 8, 2024, in European Patent Application No. 21782145.
Visscher et al., "Face Masks for Noninvasive Ventilation: Fit, Excess Skin Hydration, and Pressure Ulcers," *Respiratory Care*, 60(11):1536-1547 (Nov. 2015).
Weber et al., "Remote Wound Monitoring of Chronic Ulcers," IEEE Transactions on Information Technology in Biomedicine, IEEE Service Center, Los Alamitos, CA, vol. 13(2):371-377 (Mar. 1, 2010).
Alanen, "Measurement of Hydration in the Stratum Corneum with the MoistureMeter and Comparison with the Corneometer," *Skin Research and Technolgy*, 10:32-37 (2004).
Alberts et al., "The Extracellular Matrix of Animals," *Molecular Biology of the Cell*, 4th ed., pp. 1065-1127 (2002).
Allman et al., "Pressure Ulcer Risk Factors Among Hospitalized Patients with Activity Limitation," *JAMA*, 273:865-870.
Anonymous, "Recommended Practices for Positioning the Patient in the Perioperative Practice Setting," in *Perioperative Standards, Recommended Practices, and Guidelines*, AORN, Inc. 525-548 (2006).
Arao et al., "Morphological characteristics of the Dermal Papillae In the Development of Pressure Sores," *World Wide Wounds* (Mar. 1999), 6 pages (obtained online).
Arimoto et al., "Non-Contact Skin Moisture Measurement Based on Near-Infrared Spectroscopy," *Applied Spectroscopy*, 58(12):1439-1446 (2004).
Australian Intellectual Property Office, Office Action issued on May 1, 2014, for corresponding Australian patent application No. 2011253253 (pp. 1-10) and pending claims (pp. 11-15) pp. 1-15.
Australian Patent Office, Office Action issued on Jun. 1, 2015, for corresponding Australian Patent Application No. 2011253253 (pp. 1-4) and claims (pp. 5-10) pp. 1-10.
Bader et al., "Effect of Externally Applied Skin Surface Forces on Tissue Vasculature," *Archives of Physical Medicine and Rehabilitation*, 67(11):807-11 (1986).

Barnes, "Moisture Meters for Use on Thin Lumber and Veneers," *Moisture Register Co.*, 1-5 (1956).
Bates-Jensen et al., "Subepidermal Moisture Predicts Erythema and Stage 1 Pressure Ulcers in Nursing Home Residents: A Pilot Study," *Journal of the American Geriatric Society*, 55:1199-1205 (2007).
Bates-Jensen et al., "Subepidermal moisture differentiates erythema and stage 1 pressure ulcers in nursing home residents," *Wound Repair Regeneration*, 16:189-197 (2008).
Bates-Jensen et al., "Subepidermal Moisture Is Associated with Early Pressure Ulcer Damage in Nursing Home Residents with Dark Skin Tones; Pilot Findings," *Journal of Wound Ostomy and Continence Nursing*, 36(3):277-284.
Bates-Jensen et al., "Subdermal Moisture Detection of Pressure Induced Tissue Damage on the Trunk: The Pressure Ulcer Detection Study Outcomes," *Wound Repair and Regeneration*, 25:502-511 (2017).
Berggren, "Capacitive Biosensors," Electroanalysis, 13(3):173-180 (2001), Wiley-VCH (publisher), Weinheim, Germany.
Bergstrand et al., "Pressure-induced Vasodilation and Reactive Hyperemia at Different Depths in Sacral Tissue Under Clinically Relevant Conditions," *Microcirculation*, 21:761-771 (2014).
Bergstrom et al., "Pressure Ulcers in Adults: Prediciton and Prevention," Clinical Practice Guideline—Quick Reference Guide for Clinicians, 117 (1992).
Black et al., "Differential Diagnosis of Suspected Deep Tissue Injury," *International Wound Journal*, 13(4):531-539 (2015).
Brem et al., "Protocol for the Successful Treatment of Pressure Ulcers," *The American Journal of Surgery*, 188 (Suppl. to Jul. 2004):9S-17S (2004).
Brem et al., "High cost of stage IV pressure ulcers," American Journal of Surgery, 200:473-477 (2010).
Brienza et al., "Friction-Induced Skin Injuries—Are They Pressure Ulcers?," *Journal of Wound Ostomy and Continence Nursing*, 42(1):62-64 (2015).
Carmo-Araujo et al., "Ischaemia and reperfusion effects on skeletal muscle tissue: morphological and histochemical studies," *International Journal of Experimental Pathology*, 88:147-154 (2007).
Ceelen et al., "Compression-induced damage and internal tissue strains are related," *Journal of Biomechanics*, 41:3399-3404 (2008).
Ching et al., "Tissue electrical properties monitoring for the prevention of pressure sore," *Prosthetics and Orthotics International*, 35(4):386-394 (2011).
Clendenin et al., "Inter-operator and inter-device agreement and reliability of the SEM Scanner," *Journal of Tissue Viability*, 24(1):17-23 (2015).
De Lorenzo et al., "Predicting body cell mass with bioimpedance by using theoretical methods: a technological review," *Journal of Applied Physiology*, 82(5):1542-1558 (1997).
De Oliveira et al., "Sub-epidermal moisture versus trandition and visual skin assessments to assess pressure ulcer risk in surgery patients," *Journal of Wound Care*, 31(3):254-264 (2022), Mark Allen Group (pub.) (obtained online).
Demarre et al., "The cost of pressure ulcer prevention and treatment in hospitals and nursing homes in Flanders: A cost-of-illness study," *International Journal of Nursing Studies*, 1-14 (2015).
Dodde et al., "Bioimpedance of soft tissue under compression," *Physiology Measurement*, 33(6):1095-1109 (2012).
Dupont, "Pyralux® FR Coverlay, Bondply & Sheet Adhesive," webpage, Retrieved from: www2.dupont.com/Pyralux/en_US/products/adhesives_films/FR/FR_films_html pp. 1-2 (2012).
DuPont, "General Specifications for Kapton Polyimide Film," Retrieved from Dupont: http://www2.dupont.com/Kapton/en_US/assets/downloads/pdf/Gen_Specs.pdf, pp. 1-7 (2012).
DuPont, "Pyralux® FR Copper-clad Laminate," webpage, Retrieved from: www2.dupont.com/Pyraluxlen_US/ productsllaminate/FR/pyralux_fr.html, pp. 1-2 (2012).
Eberlein-Gonska et al., "The Incidence and Determinants of Decubitus Ulcers in Hospital Care: An Analysis of Routine Quality Management Data at a University Hospital," *Deutsches Arzteblatt International*, 110(33-34):550-556 (2013).
European Patent Office, ESSR issued on Aug. 22, 2014, for corresponding European Patent Application No. 11781061.4 (pp. 1-7) and pending claims (pp. 3-10) pp. 1-10.

(56) References Cited

OTHER PUBLICATIONS

European Patent Office, Office Action issued on Jul. 13, 2015, for corresponding European Patent Application No. 11781061.4 (pp. 1-5) and claims (pp. 6-9) pp. 1-9.
Extended European Search Report mailed Aug. 30, 2016, in European Patent Application No. 16169670.
Extended European Search Report mailed Oct. 18, 2016, in European Patent Application No. 16166483.4.
Extended European Search Report mailed Mar. 13, 2017, in European Patent Application No. 16196899.5.
Extended European Search Report mailed Oct. 25, 2019, in European Patent Application No. 19186393.5.
Extended European Search Report mailed Nov. 19, 2019, in European Patent Application No. 19190000.0.
Extended European Search Report mailed Feb. 6, 2020, in European Patent Application No. 18748733.5.
Extended European Search Report mailed Feb. 10, 2020, in European Patent Application No. 18748025.6.
Extended European Search Report mailed Feb. 10, 2020, in European Patent Application No. 18748512.3.
Extended European Search Report mailed Jun. 24, 2020, in European Patent Application No. 18747707.0.
Extended European Search Report mailed Mar. 17, 2022, in European Patent Application No. 19838240.0.
Extended European Search Report mailed May 24, 2022, in European Patent Application No. 19871332.3.
Extended European Search Report mailed Feb. 1, 2023, in European Patent Application No. 22211200.
Extended European Search Report mailed Nov. 7, 2023, in European Patent Application No. 23188775.3.
Ford, "Hospice Wins Award for Innovation in Pressure Ulcer Prevention," *Nursing Times*, downloaded and printed on Apr. 18, 2020, from https://www.nursingtimes.net/news/research-and-innovation/hospice-wins-award-for-innovation-in-pressure-ulcer-prevention-30-11-2018/ (2018).
Gabriel et al., "The dielectric properties of biological tissuer: II. Measurments in the frequency range 10 Hz to 20 GHz," *Physics in Medicine and Biology*, 41:2251-69 (1996).
Gabriel, "Compilation of the Dielectric Properties of Body Tissues of Rf and Microwave Frequencies Report," Occupational and Environmental Health Directorate, (1996).
Gardiner et al., "Incidence of hospital-acquired pressure ulcers—a population-based cohort study," *International Wound Journal*, 11(6):696-700 (2014).
Gershon et al., "SEM Scanner Readings to Assess Pressure Induced Tissue Damage," Proceedings of the 17th Annual European Pressure Ulcer Advisory Panel (EPUAP) meeting, Stockholm, Sweden (2014).
Gonzalez-Correa et al., "Electrical bioimpedance readings increase with higher pressure applied to the measureing probe," *Physiology Measurement*, 26:S39-S47 (2005).
Great Britain Search Report dated Apr. 27, 2020, in Great Britain Patent Application No. GB2002889.0.
Great Britain Search Report dated Jun. 28, 2021, in Great Britain Patent Application No. GB2106848.1.
Great Britain Search Report dated Feb. 9, 2022, in Great Britain Patent Application No. GB218088.0.
Great Britain Search Report dated Feb. 14, 2022, in Great Britain Patent Application No. GB2118092.2.
Guihan et al., "Assessing the feasibiligy of subepidermal moisture to predict erythema and stage 1 pressure ulcers in persons with spinal cord injury: A pilot study," *Journal of Spinal Cord Medicine*, 35(1):46-52 (2012).
Hamazoto et al., "Estimate of Burn Depth by Non-Invasive Capacitance Measurement," *Japan Soc. ME & BE*, 42:266 (Jun. 2003).
Harrow, "Subepidermal moisture surrounding pressure ulcers in persons with spinal cord injury: A pilot study," *Journal of Spinal Cord Medicine*, 37(6):719-728 (2014).
Hou, "Section IV. Osteofascial Compartment Syndrom," *Limbs Trauma*, 7:215-217 (2016), Hubei Science & Technology Publishing House (pub.), Wuhan, China.
Houwing et al., "Pressure-induced skin lesions in pigs: reperfusion injury and the effects of vitamin E," *Journal of Wound Care*, 9(1):36-40 (2000).
Huang et al., "A device for skin moisture and environment humidity detection," Sensors and Actuators B: Chemical, 206-212 (2008).
International Search Report and Written Opinion mailed Feb. 9, 2012, for International Patent Application No. PCT/US2011/035618.
International Search Report and Written Opinion mailed Jul. 22, 2016, for International Patent Application No. PCT/US2016/28515.
International Search Report and Written Opinion mailed Jul. 26, 2016, for International Patent Application No. PCT/US2016/28516.
International Search Report mailed Apr. 12, 2018, isssued in International Patent Application No. PCT/US2018/016731.
International Search Report mailed Apr. 12, 2018, isssued in International Patent Application No. PCT/US2018/016738.
International Search Report mailed Apr. 26, 2018, isssued in International Patent Application No. PCT/US2018/016741.
International Search Report mailed Jul. 12, 2018, isssued in International Patent Application No. PCT/US2018/016736.
International Search Report mailed Sep. 10, 2018, isssued in International Patent Application No. PCT/US2018/038055.
International Search Report mailed Jan. 29, 2019, isssued in International Patent Application No. PCT/US2018/061494.
International Search Report mailed Feb. 5, 2019, isssued in International Patent Application No. PCT/US2018/064527.
International Search Report mailed Feb. 11, 2019, isssued in International Patent Application No. PCT/US2018/061497.
International Search Report mailed May 29, 2019, isssued in International Patent Application No. PCT/US2019/017226.
International Search Report mailed Mar. 9, 2020, isssued in International Patent Application No. PCT/US2019/055655.
International Search Report mailed Dec. 8, 2020, issued in International Patent Application PCT/US2020/051134.
Internatioal Search Report mailed Aug. 17, 2021, issued in International Patent Application PCT/US2021/023818.
International Search Report mailed May 13, 2022, issued in International Patent Application PCT/US2022/014913.
International Search Report mailed Aug. 2, 2022, issued in International Patent Application PCT/US2022/025508.
International Search Report mailed Aug. 15, 2022, issued in International Patent Application PCT/US2022/019338.
Jan et al., "Local cooling reduces skin ischemia under surface pressure in rats: an assessment by wavelet analysis of laser Doppler blood flow oscillations," *Physiology Measurement*, 33(10):1733-1745 (2012).
Jaskowski, "Evaluation of the Healing Process of Skin Wounds by Means of Skin Absolute Valve of Electrical Impedance," *Dermatol. Mon.schr.*, 172(4):223-228 (1986).
Jiang et al., "Ischemia-Reperfusion Injury-Induced Histological Changes Affecting Early Stage Pressure Ulcer Development in a Rat model," *Ostomy Wound Management*, 57:55-60 (2011).
Jiang et al., "Expression of cytokines, growth factors and apoptosis-related signal molecules in chronic pressure ulcer wounds healing," *Spinal Cord*, 52(2):145-151 (2014).
Jiricka et al., "Pressure Ulcer Risk factors in a ICU Population," *American Journal of Critical Care*, 4:361-367 (1995).
Kanai et al., "Electrical measurement of fluid distribution in legs and arms," *Medical Progress through Technology Journal*, 12:159-170 (1987).
Kasuya et al., "Potential application of in vivo imaging of impaired lymphatic duct to evaluate the severity or pressure ulcer in mouse model," *Scientific Reports*, 4:4173 (7 pages) (2014).
Lee, "CapSense Best Practices," Application Note 2394, 1-10 (2007).
Liu et al., "A Systematic Review of Electrical Stimulation for Pressure Ulcer Prevention and Treatment in People with Spinal Cord Injuries," *The Journal of Spinal Cord Medicine*, 37(6):703-718 (2014).

(56) References Cited

OTHER PUBLICATIONS

Loerakker et al., "Temporal Effects of Mechanical Loading on Deformaton-Induced Damage in Skeletal Muscle Tissue," *Annual Review of Biomedical Engineering*, 38(8):2577-2587 (2010).
Loerakker et al., "The effect of deformation, ischemia, and reperfusion on the development of muscle damage during prolonged loading," *Journal of Applied Physiology*, 111(4):1168-1177 (2011).
Lyder et al., "Quality of Care for Hospitalized Medicare Patients at Risk for Pressure Ulcers," *Archives of International Medicine*, 161:1549-1554 (2001).
Martinsen, "Bioimpedance and Bioelectricity Basics," Elsevier Academic Press, Chapters 1 and 10 (2015).
Mathiesen et al., "Are labour-intensive effects to prevent pressure ulcers cost-effective?" *Journal of Medical Economics*, 16(10):1238-1245 (2013).
Matthie et al., "Analytic assessment of the various bioimpedance methods used to estimate body water," *Journal of Applied Physiology*, 84(5):1801-1816 (1998).
Miller et al., "Lymphatic Clearance during Compressive Loading," *Lymphology*, 14(4):161-166 (1981).
Moore et al., "A randomised controlled clinical trial of repositioning, using the 30° tilt, for the prevention of pressure ulcers," *Journal of Clinical Nursing*, 20:2633-2644 (2011).
Moore et al., "Pressure ulcer prevalence and prevention practices in care of the older person in the Republic of Ireland," *Journal of Clinical Nursing*, 21:362-371 (2012).
Moore et al., "A review of PU prevalence and incidence across Scandinavia, Iceland and Ireland (Part I)", *Journal of Wound Care*, 22(7):361-362, 364-368 (2013).
Moore et al., "Subepidermal Moisture (SEM) and Bioimpedance: A Literature Review of a Novel Method for Early Detection of Pressure-Induced Tissue Damage (Pressure Ulcers)," *International Wound Journal*, 14(2):331-337 (2016).
Moore, "Using SEM (Sub Epidermal Moisture) Measurement for Early Pressure Ulcer Detection," Institute for Pressure Injury Prevention, WCICT 2017 (Jun. 20-21), Manchester, UK, 7 pp., available at www.pressureinjuryprevention.com/wp-content/uploads/2017/07/ipip_Moore_Sub_Epidermal_Moisture_notes.pdf (2017) (obtained online).
Moore et al., "SEM Scanner Made Easy," *Wounds International*, pp. 1-6, available at www.woundsinternational.com (2018).
Mulasi, "Bioimpedance at the Bedside: Current Applications, Limitations, and Opportunities," *Nutritional Clinical Practice*, 30(2):180-193 (2015).
Musa et al., "Clinical impact of a sub-epidermal moisture scanner: what is the real-world use?," *J. Wound Care*, 30(3):2-11 (2021), Mark Allen Group (pub.) (obtained online).
National Pressure Ulcer Advisory Panel et al., "Prevention and Treatment of Pressure Ulcers: Clinical Practice Guideline," Cambridge Media, (2014).
Nixon et al., "Pathology, diagnosis, and classification of pressure ulcers: comparing clinical and imaging techniques," *Wound Repair and Regeneration*, 13(4):365-372 (2005).
Nuutinen et al., "Validation of a new dielectric device to assess changes of tissue water in skin and subcutaneous fat," *Physiological Measurement*, 25:447-454 (2004).
O'Goshi, "Skin conductance; validation of Skicon-200EX compared to the original model, Skicon-100," *Skin Research and Technolgy*, 3:13-18 (2007).
Oliveira, "The Accuracy of Ultrasound, Thermography, Photography and Sub-Epidermal Moisture as a Predictor of Pressure Ulcer Presence—a Systematic Review," RCSI, School of Nursing thesis (2015).
Oomens et al., "Pressure Induced Deep Tissue Injury Explained," *Annual Review of Biomedical Engineering*, 43(2):297-305 (2015).
Pang et al. (eds.) *Diagnosis and Treatment of Diabetes*, China Press of Traditional Chinese Medicine (publisher), Beijing, China, pp. 466-468 (Oct. 2016), with English Translation.
Parital European Search Report dated Sep. 6, 2023, in European Application No. 23188775.3.

Ross et al., "Assessment of Sub-Epidermal Moisture by Direct Measurement of Tissue Biocapacitance," *Medical Engineering & Physics*, 73:92-99 (Jul. 26, 2019).
Rotaru et al., "Friction between Human Skin and Medical Textiles for Decubitus Prevention," *Tribology International*, 65:91-96 (2013).
Saxena, *The Pocket Doctor: Obstetrics & Gynecology*, pp. 76-77 (2017), Tianjin Science & Technology Tranlsation & Publishing Co. Ltd. (pub.), Tianjin, China.
Scallan et al., "Chapter 4: Pathophysiology of Edema Formation," Capillary Fluid Exchange: Regulation, Functions, and Pathology, 47-61 (2010).
Schultz et al., "Extracellular matrix: review of its role in acute and chronic wounds," World Wide Wounds, 1-20 (2005).
Schwan, "Electrical properties of tissues and cells," *Advances in Biology and Medical Physics*, 15:148-199 (1957).
Seibert et al., "Technical Expert Panel Summary Report: Refinement of a Cross-Setting Pressure Ulcer/Injury Quality Measure for Skilled Nursing Facilities, Impatient Rehabilitation Facilities, Long-Term Care Hospitals, and Home Health Agencies," RTI International Abt Associates, CMS Contract No. HHSM-500-2013-130151, 49 pp. (Aug. 2019).
Sener et al., "Pressure ulcer-induced oxidative organ injury is ameliorated by beta-glucan treatment in rats," *International Immunopharmacology*, 6(5):724-732 (2006).
Sewchuck et al., "Prevention and Early Detection of Pressure Ulcers in Patients Undergoing Cardiac Surgery," *AORN Journal*, 84(1):75-96 (2006).
Sprigle et al., "Analysis of Localized Erythema Using Clinical Indicators and Spectroscopy," *Ostomy Wound Management*, 49:42-52 (2003).
Stekelenburg et al., "Role of ischemia and deformation in th eonset of compression-induced deep tissue injury: MRI-based studies in a rat model," *Journal of Applied Physiology*, 102:2002-2011 (2007).
Stekelenburg et al., "Deep Tissue Injury: How Deep is Our Understanding?" *Archives of Physical Medicine Rehabilitation*, 89(7):1410-1413 (2008).
Supplementary Partial European Search Report dated Jan. 27, 2020, in European Patent Appliation No. 18747707.
Supplementary European Search Report dated Jul. 13, 2021, in European Patent Appliation No. 18887039.
Supplementary European Search Report dated Oct. 1, 2021, in European Patent Appliation No. 19751130.
Supplementary Partial European Search Report dated Jan. 10, 2024, in European Patent Appliation No. 21782145.
Swisher et al., "Impedance sensing device enables early detection of pressure ulcers in vivo," *Nature Communications*, 6:6577-6584 (2015).
Thomas et al., "Hospital-Acquired Pressure Ulcers and Risk of Death," *Journal of the American Geriatrics Society*, 44:1435-1440 (1996).
Thomas, "Prevention and Treatment of Pressure Ulcers," *J. Am. Med. Dir. Assoc.*, 7:46-59 (2006).
Truong et al., "Pressure Ulcer Preventation in the Hospital Setting Using Silicone Foam Dressings," *Cureus*, 8(8):e730, pp. 1-6 (2016).
Tur et al., "Topical Hydrogen Peroxide Treatment of Ischemic Ulcers in the Guinea Pig: Blood Recruitment in Multiple Skin Sites," *J. Am. Acad. Dermatol.*, 33:217-221 (1995).
Valentinuzzi et al., "Bioelectrical Impedance Techniques in Medicine. Part II: Monitoring of Physiological Events by Impedance," *Crititcal Reviews in Biomedical Engineering*, 24(4-6):353-466 (1996).
Vangilder et al., "Results of Nine International Pressure Ulcer Prevalence Surveys: 1989 to 2005," *Ostomy Wound Management*, 51(2):40-54 (2008).
Vowden et al., "Diabetic Foot Ulcer or Pressure Ulcer? That Is the Question," *The Diabetic Foot Journal*, 18:62-66 (2015).
Wagner et al., "Bioelectrical Impedance as a Discriminator of Pressure Ulcer Risk," *Advances in Wound Care*, 9(2):30-37 (1996).
Wang et al., "A Wireless Biomedical Insturment for Evidence-Based Tissue Wound Characterization," *Wireless Health*, pp. 222-223 (2010).
Wang, "Biomedical System for Monitoring Pressure Ulcer Development," UCLA Electronic Theses and Dissertations, California, USA, pp. 1-123 (2013).

(56) References Cited

OTHER PUBLICATIONS

Watanabe et al., "CT analysis of the use of the electrrical impedance technique to estimate local oedema in the extremities in patients with lymphatic obstruction," *Medical and Biological Engineering and Computing*, 36(1):60-65 (1198).

Weiss, "Tissue destruction by neutrophils," *The New England Journal of Medicine*, 320(6):365-76 (1989).

Yang, *Handbook of Practical Burn Surgery*, p. 48 (2008), People's Military Medical Press (pub.), Beijing, China.

Zanibbi, "Pattern Recognition: An Overview," downloaded from https://www.cs.rit.edu/~rlaz/prec20092/slides/Overview.pdf, 30 pp. (2010).

Bluestein et al., "Pressure Ulcers: Prevention, Evaluation, and Management," *Am. Fam. Physician*, 78(10):1186-1194 (Nov. 15, 2008).

De Oliveira et al., "The accuracy of ultrasound thermography, photography and sub-epidermal moisture as a predictor of pressure ulcer presence—a systematic review," unsigned thesis submitted to the School of Postgraduate Studies, Faculty of Medicine and Health Sciences, Royal College of Surgeons in Ireland, 316 pp. (2015), retrieved from http://pstorage-rcsi-9048708668.s3.amazonaws.com/19329779/Theaccuracyofultrasoundthermographyphotographyandsubepi.pdf.

Extended European Search Report completed Jan. 1, 2025, in European Patent Application No. 22767802.6.

Extended European Search Report completed Jan. 3, 2025, in European Patent Application No. 24214401.2.

Great Britain Search Report dated Oct. 21, 2024, in Great Britain Patent Application No. GB2411677.4.

National Institute for Health and Care Excellence ("NICE"), "Pressure Ulcers: Prevention and Management," *Clinical Guideline*, 11 pp. (Apr. 23, 2014).

Reid et al., "Pressure Ulcer Prevention and Treatment: Use of Prophylactic Dressings," *Chronic Wound Care Management and Research*, 3:117-121 (Oct. 11, 2016).

Stekelenburg et al., "Compression-Induced Tissue Damage: Animal Models," in *Pressure Ulcer Research*, Springer-Verlag, Berlin/Heidelberg, pp. 187-204 (Jan. 1, 2005).

Vapiwala et al., "Enhancing Career Paths for Tomorrow's Radiation Oncologiests," *International Journal of Radiation: Oncology Biology Physics*, 105(1):52-63 (May 22, 2019) (Pergamon Press).

\* cited by examiner

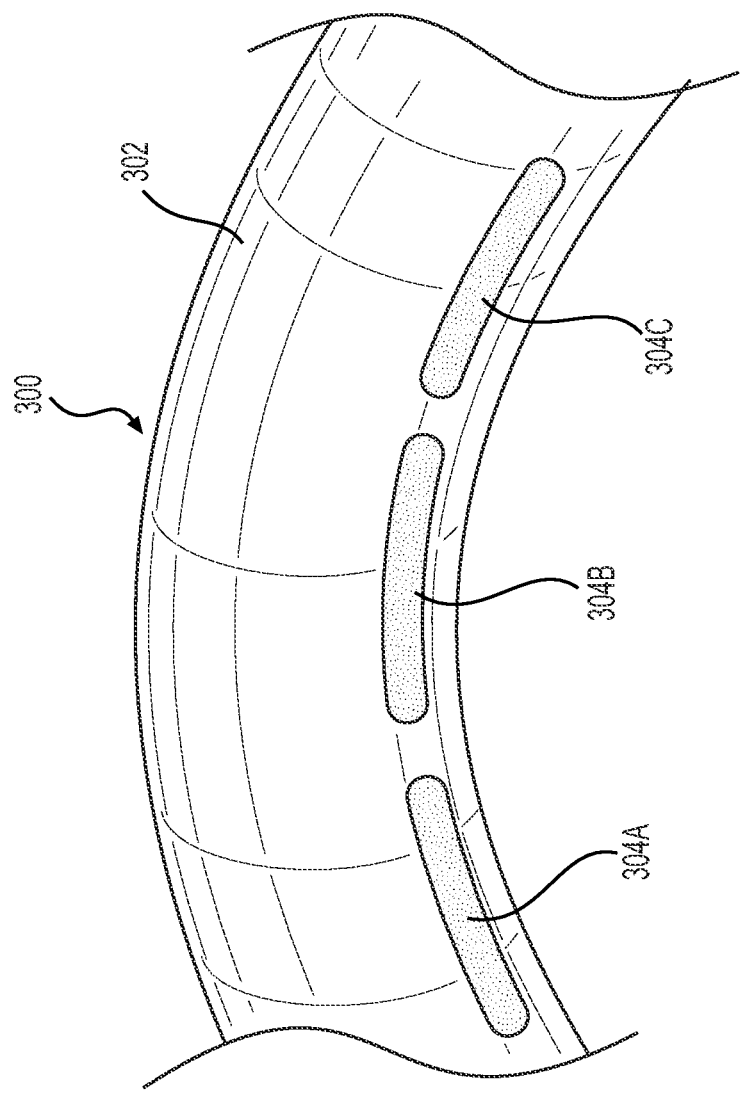

DETECTION OF TISSUE DAMAGE

CROSS-REFERENCE TO RELATED APPLICATION

This application is a continuation of U.S. Non-Provisional application Ser. No. 18/047,084 filed Oct. 17, 2022, which is a continuation of U.S. Non-Provisional application Ser. No. 16/271,040 filed Feb. 8, 2019, which claims the benefit of U.S. Provisional Application No. 62/628,676, which was filed on Feb. 9, 2018, the entirety of each of which is incorporated herein by reference.

FIELD

The present disclosure provides methods and apparatus for detecting tissue damage through measurement of Sub-Epidermal Moisture (SEM) and evaluation of those measurements.

BACKGROUND

The skin is the largest organ in the human body. It is readily exposed to different kinds of damages and injuries. When the skin and its surrounding tissues are unable to redistribute external pressure and mechanical forces, ulcers may be formed. Prolonged continuous exposure to even modest pressure, such as the pressure created by the body weight of a supine patient on their posterior skin surfaces, may lead to a pressure ulcer.

Patients may be required to use a medical device for an extended period of time to treat a particular condition. Some devices are in contact with portions of the patient's body, for example a tube feeding air to a nasal cannula. Patients who are lying prone in a bed may have devices laying on their body, in some cases taped to the skin to hold the device in place. The long-term pressure applied by these devices may be low but the extended period of application may lead to tissue damage that, left untreated, may progress to an open ulcer.

SUMMARY

In an aspect, the present disclosure provides for, and includes, an apparatus for detecting tissue damage proximate to a point of contact between a medical device and a patient's skin, comprising: a first electrode and a second electrode configured to measure a level of sub-epidermal moisture (SEM) in tissue proximate to the point of contact, an electronics package individually connected to the first and second electrodes and configured to measure a capacitance between the first and second electrodes.

In an aspect, the present disclosure provides for, and includes, a method for detecting tissue damage proximate to a point of contact between a medical device and a patient's skin, comprising the steps of: measuring a plurality of sub-epidermal moisture (SEM) values of tissue proximate to the point of contact at incremental times, comparing the plurality of SEM values, and determining if there is a significant increase in the SEM that indicates that there is tissue damage.

BRIEF DESCRIPTION OF THE DRAWINGS

Aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

FIG. 5C is an enlarged view of a portion of the device of FIG. 5B, in accordance with the present disclosure.

DETAILED DESCRIPTION

Figure 1:
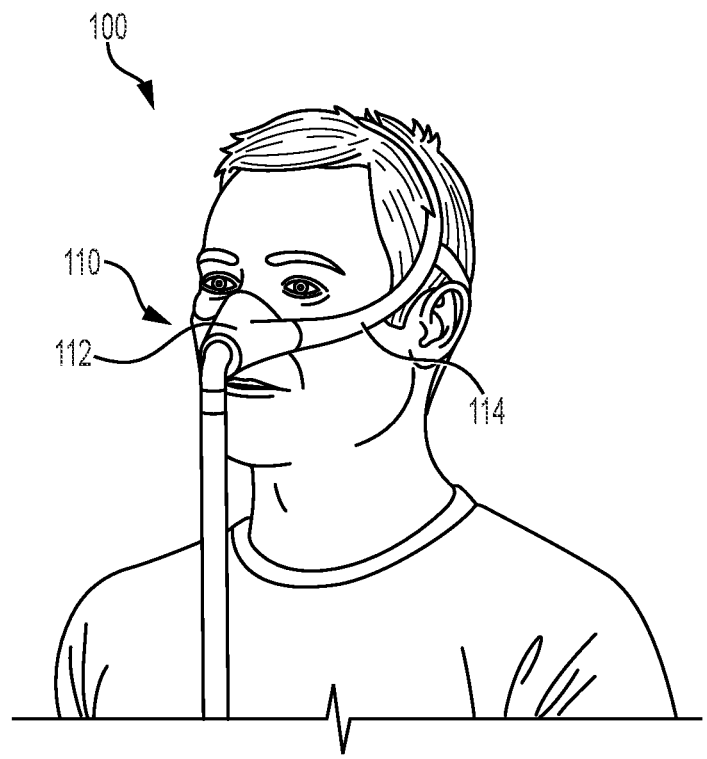
FIG. 1 depicts a patient wearing a Continuous Positive Airway Pressure (CPAP) mask.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations, and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

U.S. patent application Ser. No. 14/827,375 discloses an apparatus that measures the sub-epidermal capacitance using a bipolar sensor, where the sub-epidermal capacitance corresponds to the moisture content of the target region of skin of a patient. The '375 application also discloses an array of these bipolar sensors of various sizes.

U.S. patent application Ser. No. 15/134,110 discloses an apparatus for measuring sub-epidermal moisture (SEM) similar to the device shown in FIG. 3, where the device emits and receives an RF signal at a frequency of 32 kHz through a single coaxial sensor and generates a bioimpedance signal, then converts this signal to a SEM value.

Both U.S. patent application Ser. Nos. 14/827,375 and 15/134,110 are incorporated herein by reference in their entireties.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present disclosure. In other words, unless a specific order of steps or actions is required for proper operation of the embodiment, the order and/or use of specific steps and/or actions may be modified without departing from the scope of the present disclosure.

As used in the description of the disclosure and the appended claims, the singular forms "a," "an," and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a SEM value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "sub-epidermal moisture" or "SEM" refers to the increase in tissue fluid and local edema caused by vascular leakiness and other changes that modify the underlying structure of the damaged tissue in the presence of continued pressure on tissue, apoptosis, necrosis, and the inflammatory process.

As used herein, a "patient" may be a human or animal subject.

As used herein, "delta" refers to a calculated difference between two SEM values.

FIG. 1 depicts a patient 100 wearing a CPAP mask 110. A CPAP system is used by individuals having difficulty in breathing while sleeping, among others. The mask 110 is worn every night for the entire time that the person is asleep, typically 7-9 hours. This repeated exposure of sensitive facial tissue, where the skin is close to bone, to long-duration low-pressure contact by the nosepiece 112 or straps 114 poses a risk of developing a pressure ulcer.

Figure 2:
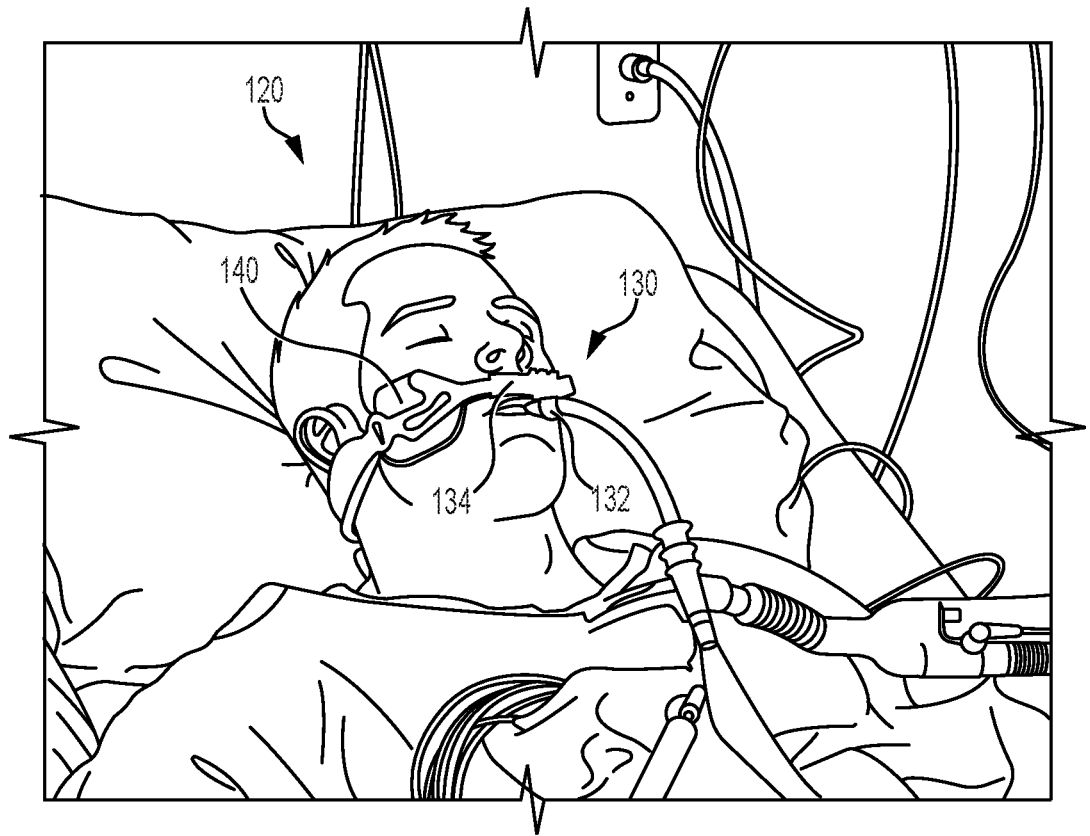
FIG. 2 depicts a patient being treated with a ventilator.

FIG. 2 depicts a patient 120 being treated with a ventilator, which includes mouthpiece 130 having, in this example, an endotracheal tube 132 held in place by a strap 134. Patients that are unable to breathe satisfactorily on their own are "put on" a respirator to ensure that their body is receiving sufficient oxygen to heal. A patient may be on a ventilator for a few hours or a few weeks, depending on the injury. Patients who are on a ventilator for extended periods of time may be put in a medically induced coma because of the discomfort of the ventilator, further reducing their mobility and increasing the risk of a pressure ulcer. In FIG. 2, a pad 140 has been placed on the cheek of the patient 120 and under the strap 134 in order to distribute pressure and protect the skin.

Figure 3A:
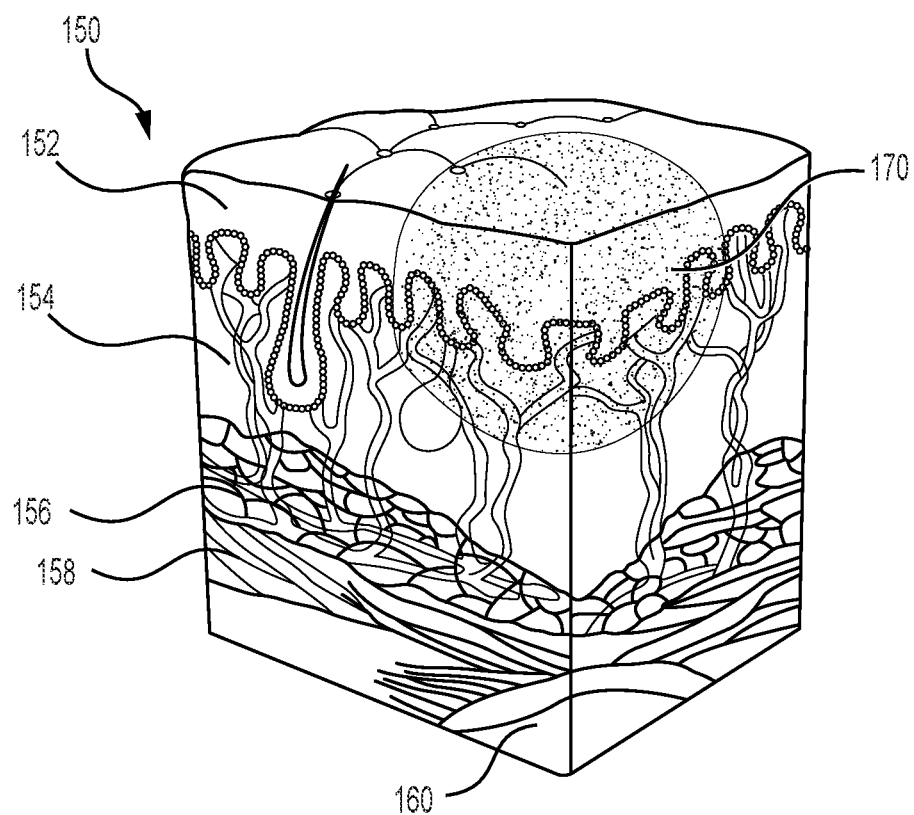
FIG. 3A illustrates the pressure-induced damage associated with a diagnosis of a stage-1 pressure ulcer.

FIG. 3A illustrates the pressure-induced damage associated with a diagnosis of a stage-1 pressure ulcer. This cutaway view of a section of skin tissue 150 shows the top layer stratum corneum, the dermis 154, a layer of fat 156 over a layer of muscle 158, and a bone 160. The darkened region 170 indicates damage to the skin penetrating from the stratum corneum 152 down into the dermis 154. The surface of the skin over region 170 may show a redness and a difference in firmness that can be identified by a trained clinician as a symptom of the damage.

Figure 3B:
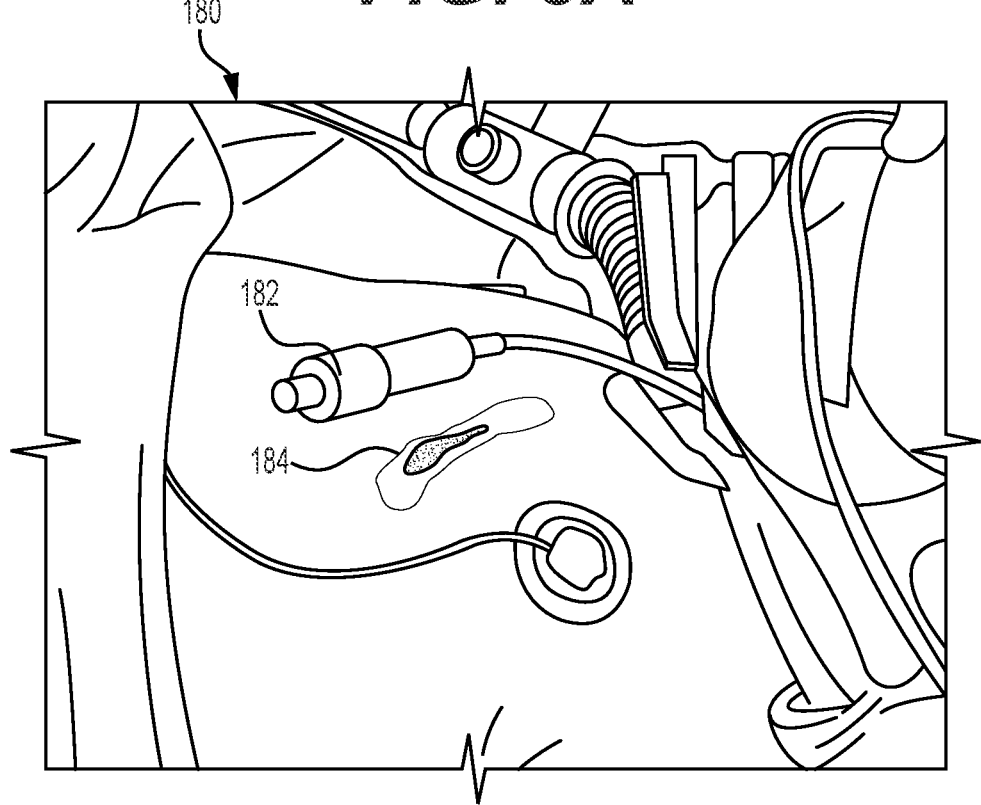
FIG. 3B depicts a patient who has developed a pressure ulcer from a medical device taped to his chest.
Figure 3C:
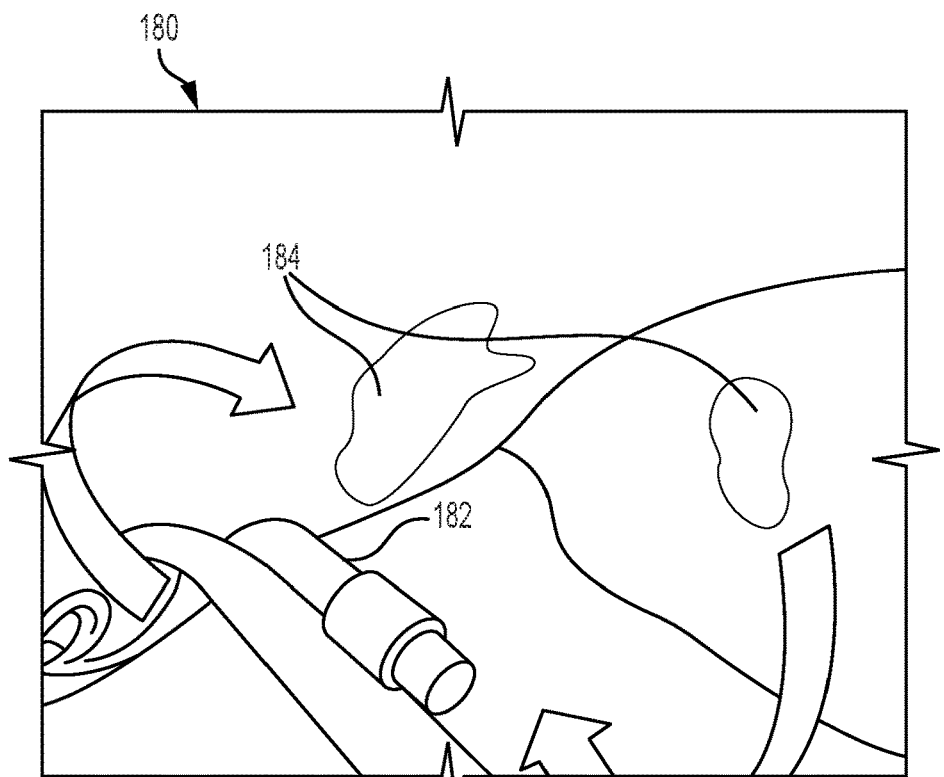
FIGS. 3C and 3D depict patients who developed pressure ulcers from urinary catheters.
Figure 3D:
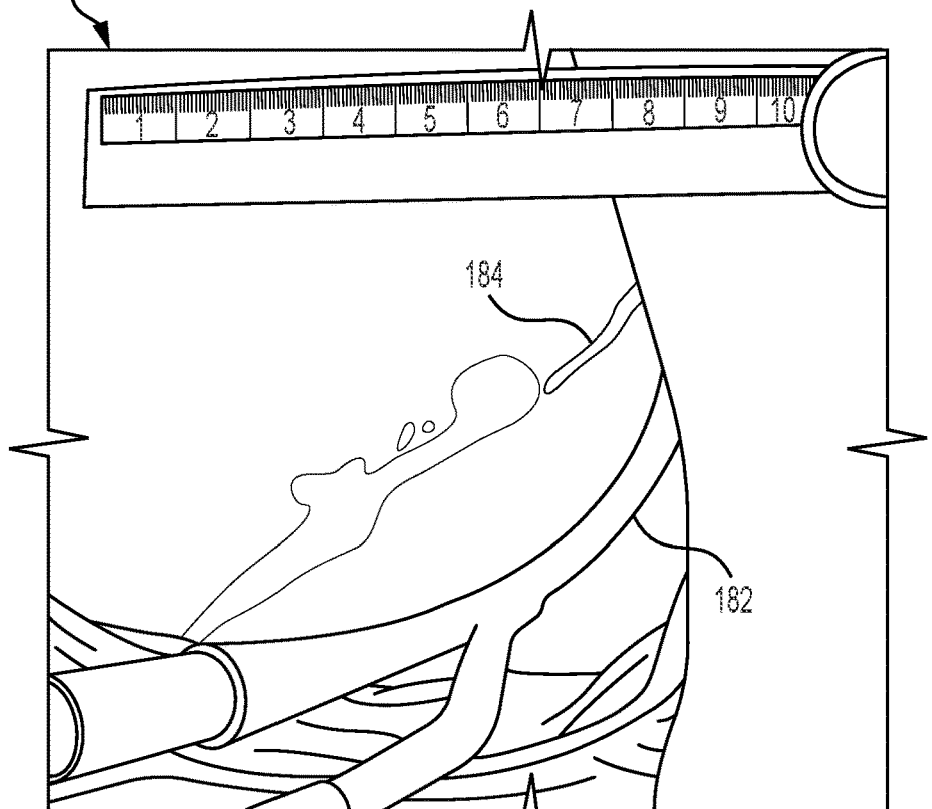

FIG. 3B depicts a patient 180 who has developed a pressure ulcer 184 from a medical device 182 taped to his chest. FIG. 3C depicts a patient 180 who has developed a pressure ulcer 184 in the pubic area from a medical device 182, which is a urinary tube. FIG. 3D depicts a patient 180 who has developed a pressure ulcer 184 in the lower abdomen area from a medical device 182, which is also a urinary tube. Development of this type of injury depends on many factors, including the amount of local pressure on the skin, whether additional pressure was created by other items laying over the device 182, and the duration of the pressure. Development of an ulcer is also affected by the condition of the patient's skin, which depends on the age of the patient and their health.

Figure 4A:
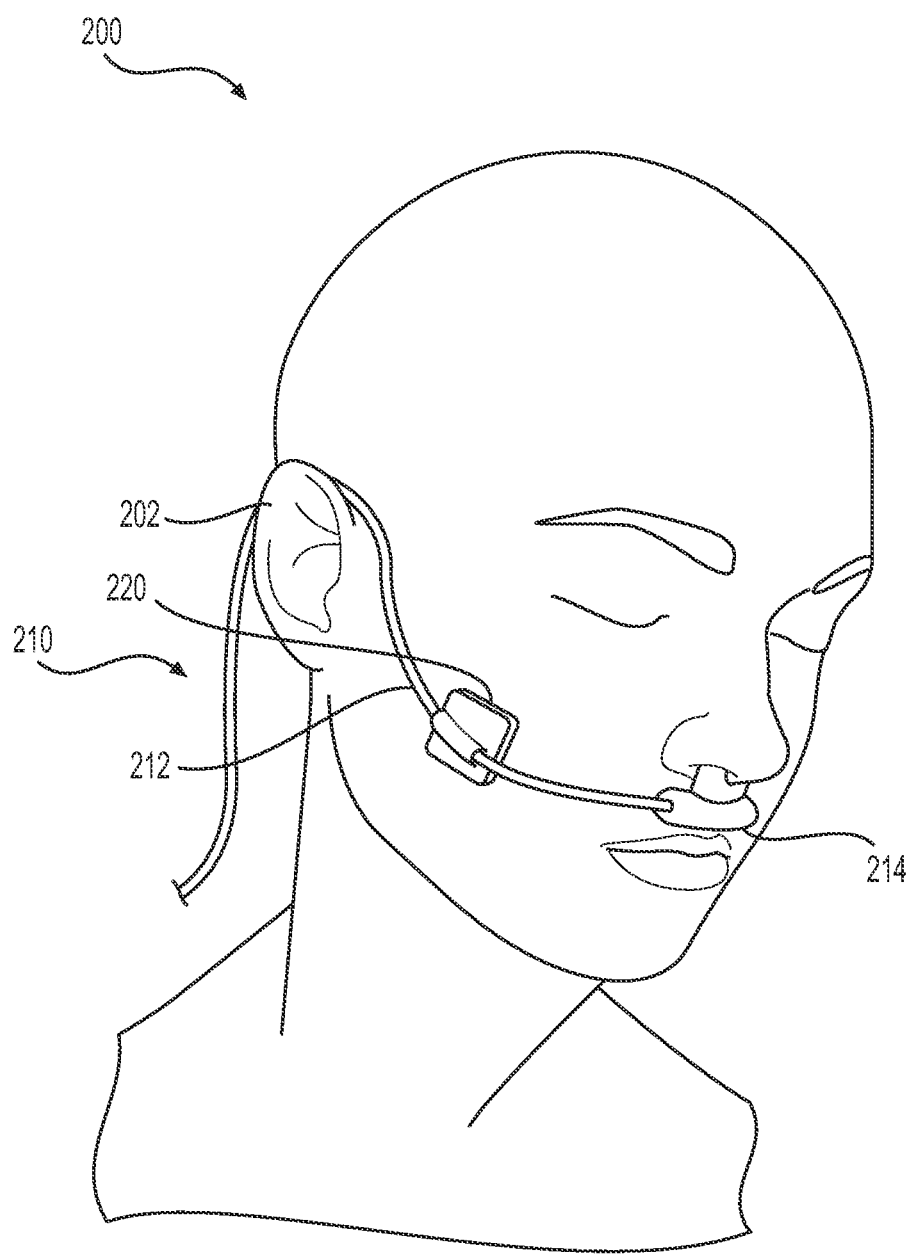
FIG. 4A depicts a patient wearing a medical device with a Sub-Epidermal Moisture (SEM) sensor, in accordance with the present disclosure.

FIG. 4A depicts a patient 200 wearing a medical device 210 with a Sub-Epidermal Moisture (SEM) sensor (not visible in FIG. 4A), in accordance with the present disclosure. There is contact between the device 210 and the patient 200 in multiple locations, such as behind the ear, along the tube 212 over the cheek, at the location of retention device 220, and at the fitting 214 where the tube 212 connects to a nasal cannula (not visible in FIG. 4A). In general, tension on the tube 212 creates pressure in many if not all of these locations.

Figure 4B:
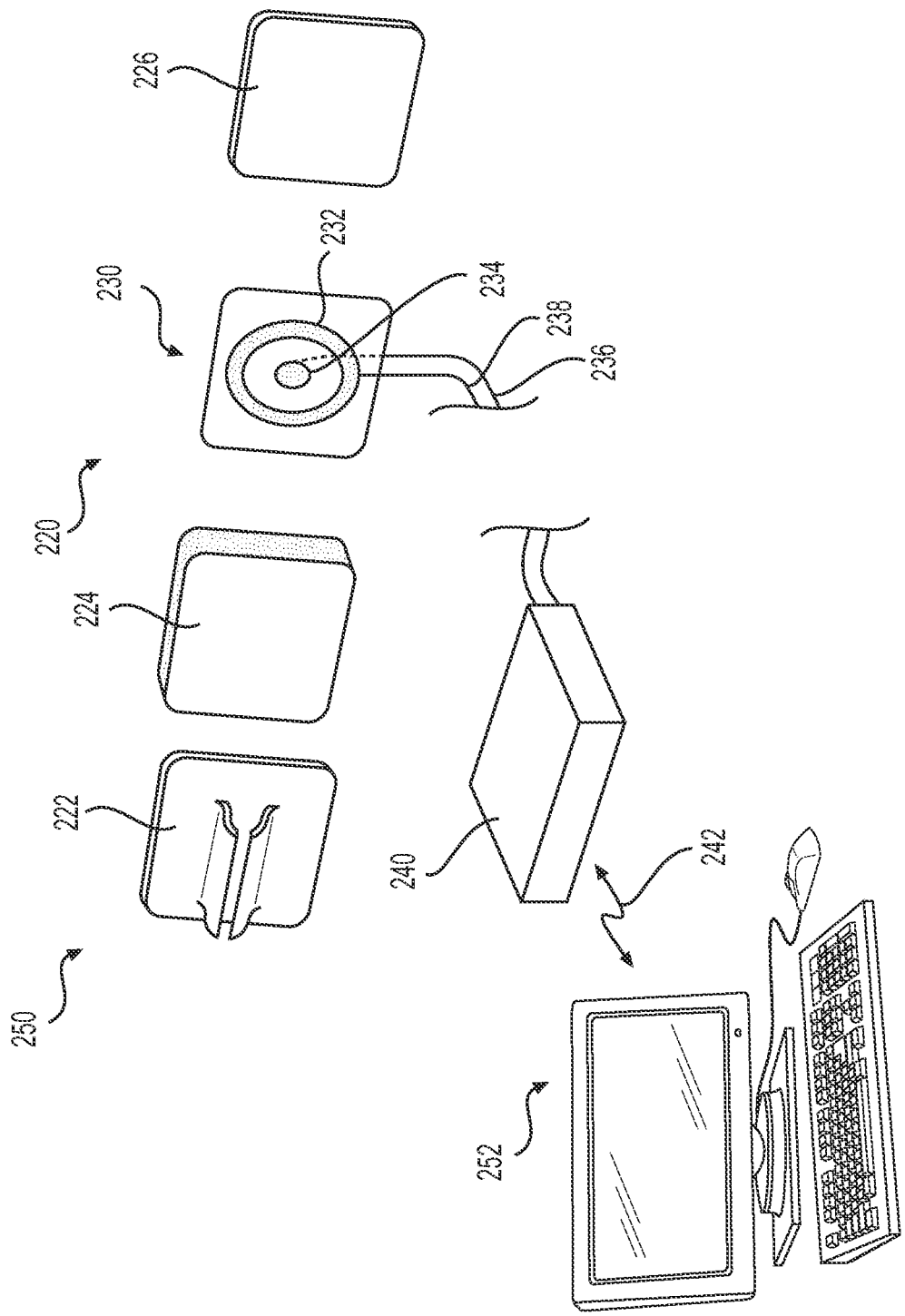
FIG. 4B depicts a SEM sensing system, in accordance with the present disclosure.

FIG. 4B depicts an example SEM sensing system 250, in accordance with the present disclosure. The system 250 includes a molded plastic clip 222 configured to attach to the tube 212, a layer of foam 224 to distribute pressure, a SEM sensor 230. In an aspect, there is a layer of adhesive 226 to attach the retention device 220 to the skin of the patient 200. The sensor 230 has electrodes 232, 234 that are connected via wires 236, 238 to electronics package 240, which is configured to make a measurement of the capacitance between the two electrodes 232, 234 and calculate a "delta" value that is, in one aspect, the difference between the highest SEM value and the lowest SEM value in a set of measurements. In an aspect, a set of measurements is taken during a single clinical evaluation. In one aspect, a set of measurements is taken over time, with the first measurement taken at the time of the first use of the medical device.

In an aspect, a calculated delta value is compared to a threshold. When the delta value exceeds the threshold, this indicates a degree of damage. There may be multiple thresholds used to evaluate multiple levels of tissue damage. In one aspect, the maximum SEM value is compared to a threshold. When the maximum value exceeds the threshold, this indicates a degree of damage.

In an aspect, a threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a threshold can be scaled by a factor or a multiple based on the values provided herein. It will be understood that a threshold is not limited by design, but rather, one of ordinary skill in the art would be capable of choosing a predetermined value based on a given unit of SEM. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In an aspect, the electronics package 240 includes devices to communicate over link 242 to computer 252, which may be a PC, a mobile tablet, a mobile phone, a server using cloud-based data storage and analysis, or other data systems. Link 242 may include a wired or wireless communication element, optical communication elements, a network that may have one or more switches and routers, and other standard data transfer devices and protocols. Link 242 may also be implemented as hardware with nonvolatile storage, for example a "thumb drive," that is loaded with data by the electronics package 240 and in turn is physically relocated and connected to the computer 252 whereupon it delivers the data. In an aspect, Link 242 provides real-time communication of recorded SEM measurements and/or calculated delta values from electronic package 240 to computer 252 to allow for real-time monitoring of ulcer development in a patient.

In one aspect, a molded plastic clip 222 of SEM sensing system 250 of the present disclosure is configured to attach to a medical device selected from the group consisting of a nasogastric tube, a feeding tube, an endotracheal tube, a tracheostomy tube, a tracheostomy collar, a nasal cannula, an IV/PICC line, a central line, a catheter, and a fecal management tube. In an aspect, adhesive 226 has a shape selected from the group consisting of substantially a square, substantially a rectangle, substantially a circle, and a polygon. In one aspect, a face of adhesive 226 has a surface area less than 25 cm$^2$, such as less than 20 cm$^2$, less than 15 cm$^2$, less than 10 cm$^2$, or less than 5 cm$^2$. In an aspect, SEM sensing system 250 has a mass of less than 5 grams, such as less than 4 grams, less than 3 grams, less than 2 grams, less than 1 gram, or less than 0.5 gram.

Figure 5A:
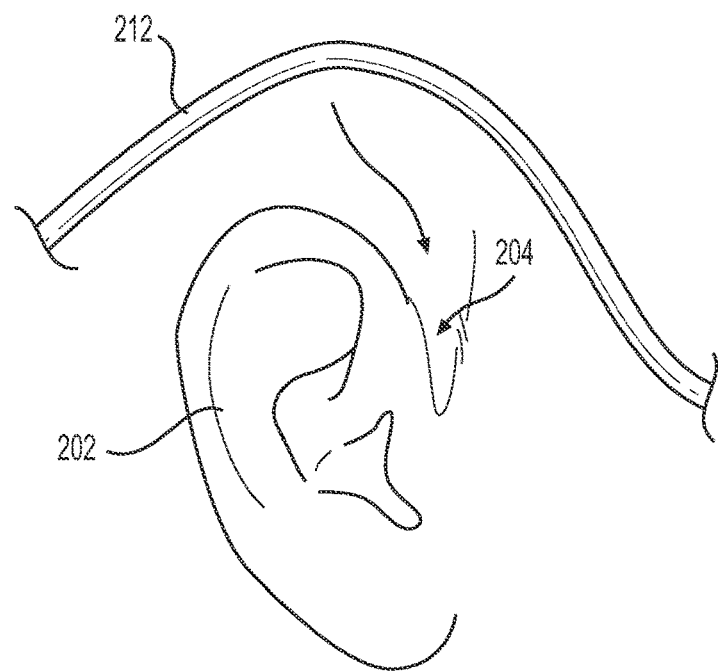
FIG. 5A illustrates how a medical device may contact a patient.

FIG. 5A illustrates how a medical device may contact a patient. The tube 212 from FIG. 4A runs over the crease 204 between a patient's ear 202 and their skull. Pressure can develop at the point of contact between tube 212 and the crease 204 due to tension in tube 212.

Figure 5B:
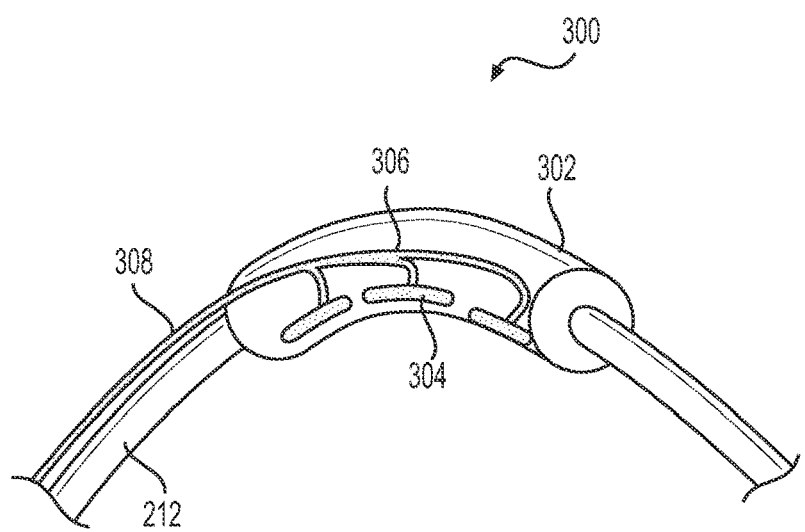
FIG. 5B depicts a SEM sensing device, in accordance with the present disclosure.

FIG. 5B depicts a SEM sensing device 300, in accordance with the present disclosure. In an aspect, the device 300 is added to a basic medical device, for example tube 212. Electrodes 304 on the external surface of the device body 302 are connected by wires 306 of cable 308 to an external electronics package (not shown in FIG. 5B). In an aspect, the device 300 comprises a processor (not visible in FIG. 5B) that does one or more of switching, sensing, and measurement. In an aspect, the processor provides wireless communication to the electronics package. In one aspect, the wireless communication to the electronics package from the electrodes occurs in real-time. In an aspect, the wireless communication to the electronics package is delayed.

FIG. 5C is an enlarged view of a portion of the device 300 of FIG. 5B, in accordance with the present disclosure. In this example, there are three electrodes 304A, 304B, and 304C that are aligned in a row on the surface of body 302, but this array of electrodes may utilize two or more electrodes that are disposed in any two-dimensional pattern. In an aspect, device 300 may comprise three or more electrodes, such as four or more electrodes, five or more electrodes, ten or more electrodes, fifteen or more electrodes, twenty or more electrodes, twenty-five or more electrodes, thirty or more electrodes, forty or more electrodes, or fifty or more electrodes.

In FIG. 5C, electrodes 304A, 304B, 304C are elongated rectangles with rounded ends, but these electrodes may be provided in any shape and size. In an aspect, electrodes 304A, 304B, and 304C may be any shape or configuration, such as point electrodes, plate electrodes, ring electrodes, hexagonal electrodes, or interdigitated finger electrodes. In this example, the long, thin aspect ratio of the electrodes over the curved body 302 provides for complete contact between each electrode 304A, 304B, 304C and the patient's skin. In one aspect, electrodes of device 300 are approximately evenly spaced apart by from about 0.1 cm to about 5 cm, such as from about 0.2 cm to about 5 cm, from about 0.3 cm to about 5 cm, from about 0.4 cm to about 5 cm, from about 0.5 cm to about 5 cm, from about 1 cm to about 5 cm, from about 1.5 cm to about 5 cm, from about 2 cm to about 5 cm, from about 2.5 cm to about 5 cm, from about 3 cm to about 5 cm, from about 3.5 cm to about 5 cm, from about 4 cm to about 5 cm, from about 4.5 cm to about 5 cm, from about 0.1 cm to about 4.5 cm, from about 0.1 cm to about 4 cm, from about 0.1 cm to about 3.5 cm, from about 0.1 cm to about 3 cm, from about 0.1 cm to about 2.5 cm, from about 0.1 cm to about 2 cm, from about 0.1 cm to about 1.5 cm, from about 0.1 cm to about 1 cm, from about 0.1 cm to about 0.9 cm, from about 0.1 cm to about 0.8 cm, from about 0.1 cm to about 0.7 cm, from about 0.1 cm to about 0.6 cm, from about 0.1 cm to about 0.5 cm, from about 0.1 cm to about 0.4 cm, from about 0.1 cm to about 0.3 cm, from about 0.1 cm to about 0.2 cm, from about 0.5 cm to about 4.5 cm, from about 1 cm to about 4 cm, from about 1.5 cm to about 3.5 cm, or from about 2 cm to about 3 cm. In an aspect, there is an insulating cover layer over each of the electrodes 304A, 304B, 304C.

Still referring to FIG. 5C, the electrodes 304A, 304B, 304C are individually coupled to the electronics package or other controlling processor such that pairs of any two electrodes may be selected to form a two-electrode sensor. With an array of electrodes, a plurality of sensors may be formed to measure capacitance over a region without moving the device 300. For example, electrodes 304A, 304B can be paired to measure the SEM in the tissue between the electrodes 304A, 304B, then electrodes 304B, 304C can be paired to measure the SEM in the tissue between the electrodes 304B, 304C.

In an aspect, device 300 of the present disclosure is configured to attach to a medical device selected from the group consisting of a nasogastric tube, a feeding tube, an endotracheal tube, a tracheostomy tube, a nasal cannula, an IV/PICC line, a central line, a catheter, and a fecal management tube. In one aspect, device 300 has a mass of less than 5 grams, such as less than 4 grams, less than 3 grams, less than 2 grams, less than 1 gram, or less than 0.5 gram.

Figure 6A:
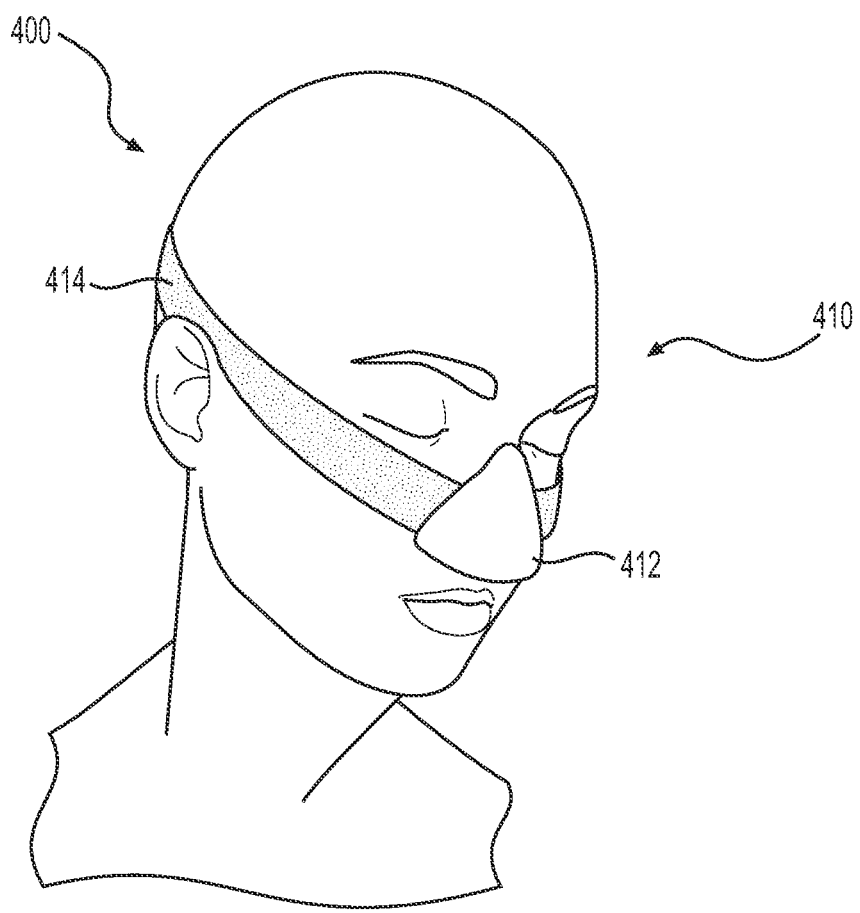
FIG. 6A depicts a patient wearing a medical device that incorporates an elastic retention strap, in accordance with the present disclosure.

FIG. 6A depicts a patient 400 wearing a medical device 410 that incorporates a retention strap 414 to hold nosepiece 412 in place, in accordance with the present disclosure. In order to function, there must be tension in the elastic strap 414 and along the contact edges of nosepiece 412.

Figure 6B:
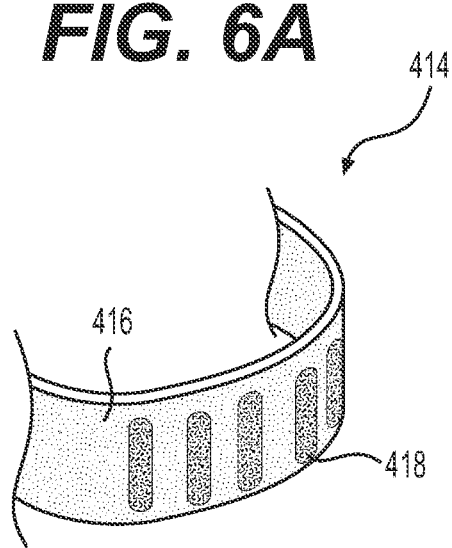
FIG. 6B is an enlarged view of a portion of the retention strap of FIG. 6A, in accordance with the present disclosure.

FIG. 6B is an enlarged view of a portion of the retention strap 414 of FIG. 6A, in accordance with the present disclosure. In this example, electrodes 418 are attached to the elastic 416 such that the electrodes 418 are in contact with the patient's skin while the device 410 is worn. In one aspect, electrodes 418 are elongated-shaped electrodes. In an aspect, similar electrodes (not shown in FIG. 6B) are located on the contact surface of the nosepiece. As described with respect to FIG. 5C, the individual electrodes of an array of electrodes 418 can be connected in various pairs to form sensors. In an aspect, the retention strap 414 includes one or more of a battery, a processor, data storage, and a communication element.

In an aspect, retention strap 414 may comprise two or more electrodes, such as three or more electrodes, four or more electrodes, five or more electrodes, ten or more electrodes, fifteen or more electrodes, twenty or more electrodes, twenty-five or more electrodes, thirty or more electrodes, forty or more electrodes, fifty or more electrodes or a hundred or more electrodes.

In one aspect, electrodes of retention strap 414 are approximately evenly spaced apart by from about 0.1 cm to about 5 cm when the retention strap is in a relaxed state, such as from about 0.2 cm to about 5 cm, from about 0.3 cm to about 5 cm, from about 0.4 cm to about 5 cm, from about 0.5 cm to about 5 cm, from about 1 cm to about 5 cm, from about 1.5 cm to about 5 cm, from about 2 cm to about 5 cm, from about 2.5 cm to about 5 cm, from about 3 cm to about 5 cm, from about 3.5 cm to about 5 cm, from about 4 cm to about 5 cm, from about 4.5 cm to about 5 cm, from about 0.1 cm to about 4.5 cm, from about 0.1 cm to about 4 cm, from about 0.1 cm to about 3.5 cm, from about 0.1 cm to about 3 cm, from about 0.1 cm to about 2.5 cm, from about 0.1 cm to about 2 cm, from about 0.1 cm to about 1.5 cm, from about 0.1 cm to about 1 cm, from about 0.1 cm to about 0.9 cm, from about 0.1 cm to about 0.8 cm, from about 0.1 cm to about 0.7 cm, from about 0.1 cm to about 0.6 cm, from about 0.1 cm to about 0.5 cm, from about 0.1 cm to about 0.4 cm, from about 0.1 cm to about 0.3 cm, from about 0.1 cm to about 0.2 cm, from about 0.5 cm to about 4.5 cm, from about 1 cm to about 4 cm, from about 1.5 cm to about 3.5 cm, or from about 2 cm to about 3 cm.

In an aspect, retention strap 414 of the present disclosure is configured to function as a tracheostomy strap. In one aspect, retention strap 414 of the present disclosure is configured to function as an abdominal binder. In an aspect, retention strap 414 of the present disclosure is configured to attach to an oxygen delivery mask. In one aspect, retention strap 414 of the present disclosure is configured to attach to an identification band.

In one aspect, a face of retention strap 414 has a surface area less than 6000 $cm^2$, such as less than 5000 $cm^2$, less than 4000 $cm^2$, less than 3000 $cm^2$, less than 2000 $cm^2$, less than 1000 $cm^2$, less than 500 $cm^2$, less than 100 $cm^2$, less than 50 $cm^2$, less than 25 $cm^2$, less than 20 $cm^2$, less than 15 $cm^2$, less than 10 $cm^2$, or less than 5 $cm^2$.

Figure 7A:
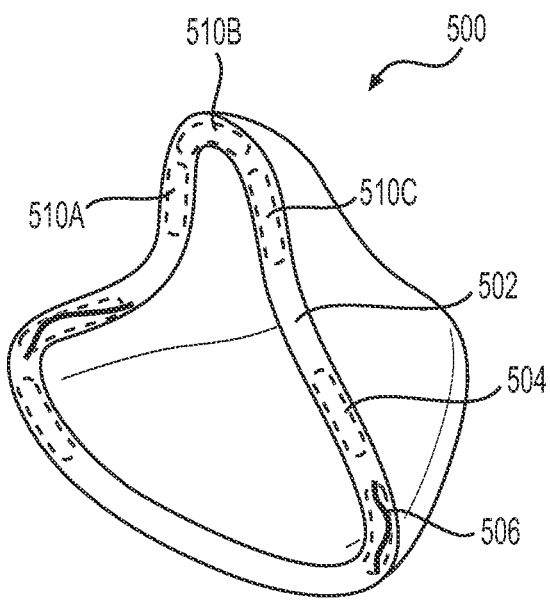
FIGS. 7A and 7B depict example medical devices with controllable pressure management elements, in accordance with the present disclosure.

FIG. 7A depicts an example medical device 500 with controllable pressure management elements, in accordance with the present disclosure. In this example, the medical device 500 is a breathing mask that is representative of all devices where the application element is in long-term contact with the skin of a patient. In an aspect, a medical device having an application element in long-term contact with the skin of a patient is a collar or a cast. In one aspect, a medical device having an application element in long-term contact with the skin of a patient is a cervical collar or a cervical cast. In this example, the pressure management elements are inflatable pockets such as pocket 504, which is shown in an inactive, e.g., deflated, state. Pocket 506, by way of comparison, is shown in an active, e.g., inflated, state. When pockets 504, 506 are configured as shown in FIG. 7A, pressure is higher in the region of pocket 506 and lower in the region of pocket 504. In an aspect, the pressure in the region of pocket 504 is low enough to allow blood flow through the tissue of this region.

In an aspect, the pressure management elements are provided in sets such as pockets 510A, 501B, and 510C. These pockets may be manipulated in a coordinated fashion to shift the levels of contact pressure between the device 500 and the skin of the patient in the regions of the pockets 510A, 510B, 510C. For example, the pocket 510B is inflated while pockets 510A, 510C are deflated, creating a relatively high contact pressure area around pocket 510B and a relatively low, e.g. lower than the nominal pressure that would be present in the absence of a pressure management element, contact pressure in the regions of pockets 510A, 510C. This relatively low contact pressure allows adequate blood flow to the tissue in that region so as to avoid tissue damage. At a different time, one or both of pockets 510A, 510C are inflated while pocket 510B is deflated, thus reducing the contact pressure in the region of pocket 510B.

In an aspect, the pockets are flexible membranes that comprise a portion of the walls of a sealed compartment that is within or on the surface of device 500. In an aspect, at least one of the walls of the pockets is stretchable. In one aspect, when the pockets are situated within the surface of device 500, the wall of device 500 that is in contact with the skin of a patient is also stretchable.

The words "force" and "pressure" are considered to be interchangeable within the context of this disclosure. A higher pressure within a pocket will apply a greater pressure over the area of the pocket, which produces a higher total force (pressure×area=force). A greater amount of fluid in the pocket does not intrinsically apply a higher pressure or force; the raised height of the pocket will cause the patient's skin to come in contact with the inflated pocket first and thereby the inflated pocket will provide a greater portion of the total force applied by the device 500 to the patient's skin and such is equivalent to providing a greater pressure and/or force.

Pockets may be fully inflated, fully deflated, or partially inflated to an intermediate pressure. In an aspect, the pockets may be inflated with a gas or a liquid or other fluid. The word "inflation" is interpreted as an indication of pressure or, equivalently, of the amount of fluid within the pocket, such that the phrase "higher inflation" includes the situation of a greater amount of fluid in the compartment.

In an aspect, the pockets are connected to a source of pressurized fluid through elements such as tubing, valves, pressure regulators (not shown in FIG. 7A) that are coupled to and controlled by a controller (not shown in FIG. 7A). In an aspect, the source of pressurized fluid may be the same source of fluid being provided to the patient through the medical device 500, for example pressurized oxygen-enriched air. In an aspect, the controller of the pressure management element is a part of the electronics package 240 of FIG. 4B.

In an aspect, the pressure management element is a mechanical element whose height can be adjusted. In an aspect, the adjustment is provided with an electrical actuator. In an aspect, the actuator comprises a piezoelectric element that causes a change in the height of the element. In an aspect, the pressure management element is a fixed height element that moves parallel to the skin of the patient such that the contact pressure is increased in the region of contact between the element and the skin and reduced in other regions.

Figure 7B:
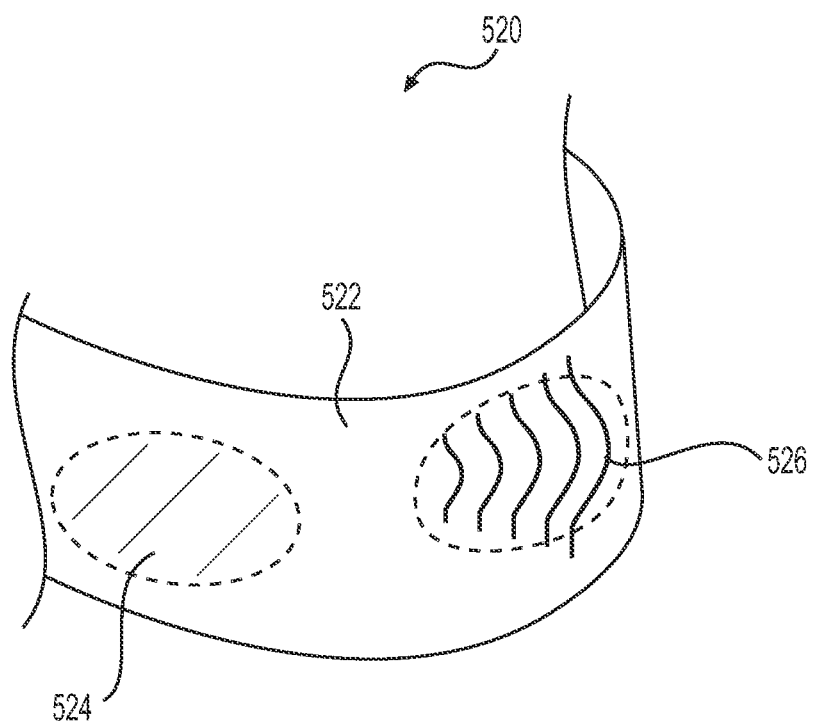

FIG. 7B illustrates another medical device that is a strap 520 similar to the strap 414 shown in FIGS. 6A and 6B. In this example, the strap 520 comprises a band 522 with pockets such as pockets 524, 526 spaced along the band 522. In this example, pocket 524 is inactive and pocket 526 is active, causing the contact pressure under pocket 526 to be higher than the contact pressure under pocket 524. In an aspect, the band 522 is overlaid with an array of electrodes 418 (not visible in FIG. 7B) such that strap 520 can both measure SEM and manage the pressure applied by the strap 520 to the patient's skin.

In an aspect, the change in inflation of the pockets is driven by an SEM reading taken, for example, by the electrodes 418 of FIG. 6B. In one aspect, the change in inflation of the pockets is driven by a delta value that is, in an aspect, the difference between the highest SEM value and the lowest SEM value in a set of measurements. In an aspect, a set of measurements includes measurements taken at a single location. In one aspect, a set of measurements includes measurements taken at multiple locations. In one aspect, a set of measurements is taken at approximately the same time, such as within 10 minutes, within 5 minutes, within 1 minute, within 30 seconds, within 10 seconds, within 5 seconds, or within 1 second. In an aspect, a delta value is calculated by the difference between the most recent SEM value and the cumulative average SEM value over a period of time. In one aspect, a cumulative average SEM value is derived from a set of SEM measurements taken since the first use of the medical device. In an aspect, a cumulative average SEM value is derived from SEM measurements taken within approximately a year, such as within 9 months, within 6 months, within 5 months, within 4 months, within 3 months, within 2 months, within 1 month, within four weeks, within three weeks, within two weeks, within one week, within 6 days, within 5 days, within 4 days, within 3 days, within 2 days, within 1 day, within 16 hours, within 12 hours, within 8 hours, within 4 hours, within 3 hours, within 2 hours, within 1 hour, within 45 minutes, within 30 minutes, within 15 minutes, within 10 minutes, or within 5 minutes.

In an aspect, the change in inflation of the pockets is driven by how a calculated delta value is compared to a threshold. When the delta value exceeds the threshold, inflation pattern of the pockets changes to shift the pressure applied to the patients. There may be multiple thresholds used to determine the inflation pattern of the pockets.

In an aspect, the change in inflation is caused by a timer that regularly shifts the pressure applied to the patient by changing the pattern of active pressure management elements, for example by inflating and deflating different pockets.

In an aspect, a series of predetermined configurations of the pressure management elements are defined and the timer configured to execute a programmed series of changes between these configurations at predefined times. In an aspect, the changes between predetermined configurations are based on SEM readings taken of the patient.

In an aspect, there is a configuration of which pockets are inflated and this default is maintained until a SEM reading indicates a problem, whereupon certain pockets are deflated or reduced in inflation height.

From the foregoing, it will be appreciated that the present invention can be embodied in various ways, which include but are not limited to the following:

Embodiment 1. An apparatus for detecting tissue damage proximate to a point of contact between a medical device and a patient's skin, comprising: a first electrode and a second electrode configured to measure a level of sub-epidermal moisture (SEM) in tissue proximate to the point of contact, an electronics package individually connected to the first and second electrodes and configured to measure a capacitance between the first and second electrodes.

Embodiment 2. The apparatus of embodiment 1, where the first and second electrodes are configured to be attached to the medical device.

Embodiment 3. The apparatus of embodiment 1 or 2, where the first and second electrodes are shaped such that the entire surface of each electrode can contact the patient's skin while the medical device is in use.

Embodiment 4. The apparatus of any one of embodiments 1 to 3, further comprising a body coupled to the first and second electrodes, the body configured to be interposed between the medical device and the patient's skin when the medical device is in use.

Embodiment 5. The apparatus of embodiment 4, where the body is further configured to be attached to the medical device.

Embodiment 6. The apparatus of any one of embodiments 1 to 5, further comprising a communication element configured to provide real-time transfer of SEM measurements to a computing unit.

Embodiment 7. The apparatus of any one of embodiments 1 to 6, where the apparatus is a clip configured to attach to a tube of the medical device.

Embodiment 8. The apparatus of embodiment 7, where the tube is selected from the group consisting of a nasogastric tube, a feeding tube, an endotracheal tube, a tracheostomy tube, a tracheostomy collar, a nasal cannula, an IV/PICC line, a catheter, and a fecal management tube.

Embodiment 9. The apparatus of any one of embodiments 1 to 6, where the apparatus is a strap configured to attach to the medical device.

Embodiment 10. The apparatus of embodiment 9, where the medical device is a mask.

Embodiment 11. The apparatus of any one of embodiments 1 to 6, where the medical device is a collar or a cast.

Embodiment 12. The apparatus of any one of embodiments 1 to 11, where the apparatus further comprises one or more pressure management elements.

Embodiment 13. The apparatus of embodiment 12, where each of the one or more pressure management elements is an inflatable pocket.

Embodiment 14. A method for detecting tissue damage proximate to a point of contact between a medical device and a patient's skin, comprising the steps of: measuring a plurality of sub-epidermal moisture (SEM) values of tissue proximate to the point of contact at incremental times, comparing the plurality of SEM values, and determining if there is a significant increase in the SEM that indicates that there is tissue damage.

Embodiment 15. The method of embodiment 14, where there is a significant increase when the largest SEM value of the plurality of SEM values is greater than the smallest SEM value of the plurality of SEM values by an amount that exceeds a threshold.

Embodiment 16. The method of embodiment 14, where there is a significant increase when the largest SEM value of the plurality of SEM values is greater than a threshold.

Embodiment 17. The method of any one of embodiments 14 to 16, where a first measurement of the SEM value is made at the time of the first use of the medical device.

Embodiment 18. The method of any one of embodiments 14 to 17, where the medical device comprises a tube selected from the group consisting of a nasogastric tube, a feeding tube, an endotracheal tube, a tracheostomy tube, a tracheostomy collar, a nasal cannula, an IV/PICC line, a catheter, and a fecal management tube.

Embodiment 19. The method of any one of embodiments 14 to 17, where the medical device is a mask.

Embodiment 20. The method of any one of embodiments 14 to 17, where the medical device is a collar or a cast.

We claim:

1. An apparatus comprising:
   a first electrode and a second electrode configured to measure a level of sub-epidermal moisture (SEM),
   an electronics package individually connected to the first and second electrodes and configured to measure a capacitance between the first and second electrodes, and
   an inflatable pocket, wherein the inflatable pocket is configured to change inflation to shift levels of contact pressure between a medical device and a patient's skin, and wherein the change in inflation of the inflatable pocket is driven by a delta value from two or more SEM readings.

2. The apparatus of claim 1, wherein the inflatable pocket is situated within the surface of the medical device.

3. The apparatus of claim 1, wherein the inflatable pocket is stretchable.

4. The apparatus of claim 1, wherein the inflatable pocket is inflated with a gas, a liquid, a pressurized fluid, or other fluid.

5. The apparatus of claim 1, wherein the delta value is calculated by the difference between the highest SEM value and the lowest SEM value in the two or more SEM readings.

6. The apparatus of claim 5, wherein the two or more SEM readings are taken at a single location.

7. The apparatus of claim 5, wherein the two or more SEM readings are taken at multiple locations.

8. The apparatus of claim 5, wherein the two or more SEM readings are taken at a single time.

9. The apparatus of claim 5, wherein the two or more SEM readings are taken over a period of time.

10. The apparatus of claim 1, wherein the delta value is calculated by the difference between the most recent SEM value and the cumulative average SEM value.

11. The apparatus of claim 10, wherein the cumulative average SEM value is derived from a set of SEM measurements taken since the first use of the medical device.

12. The apparatus of claim 1, wherein the inflation change of the inflatable pocket is maintained until an SEM reading indicates a degree of tissue damage.

13. The apparatus of claim 12, wherein the inflation of the inflatable pocket is reduced when the SEM reading indicates a degree of tissue damage.

14. The apparatus of claim 1, wherein the inflation change of the inflatable pocket is driven by a timer.

15. The apparatus of claim 1, wherein the inflatable pocket comprises a flexible membrane.

16. An apparatus comprising:
   a first electrode and a second electrode configured to measure a level of sub-epidermal moisture (SEM),
   an electronics package individually connected to the first and second electrodes and configured to measure a capacitance between the first and second electrodes, and
   an inflatable pocket, wherein the inflatable pocket is configured to change inflation to shift levels of contact pressure between a medical device and a patient's skin, and wherein the inflation change of the inflatable pocket is driven by a delta value compared to a threshold.

17. The apparatus of claim 16, wherein when the delta value exceeds the threshold, the inflation pocket changes to shift the contact pressure applied to the patient.

18. The apparatus of claim 16, wherein when the delta value exceeds the threshold, this indicates a degree of tissue damage.

19. The apparatus of claim 18, wherein there are multiple thresholds to indicate multiple degrees of tissue damage.

* * * * *